United States Patent
Anderson et al.

(10) Patent No.: US 6,605,172 B1
(45) Date of Patent: Aug. 12, 2003

(54) METHOD OF MAKING A BREATHABLE AND LIQUID IMPERMEABLE WEB

(75) Inventors: Barry Jay Anderson, Reading, OH (US); Todd Leon Mansfield, Cincinnati, OH (US); George Christopher Dobrin, Mason, OH (US); Suna Polat, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 199 days.

(21) Appl. No.: 09/669,329

(22) Filed: Sep. 25, 2000

Related U.S. Application Data
(60) Provisional application No. 60/156,900, filed on Sep. 30, 1999.

(51) Int. Cl.[7] .................................................. D02J 1/06
(52) U.S. Cl. ...................... 156/199; 264/288.8; 264/257
(58) Field of Search ....................... 156/199; 264/288.8, 264/257

(56) References Cited

U.S. PATENT DOCUMENTS

| | | | |
|---|---|---|---|
| 3,690,977 A | 9/1972 | Loft et al. | |
| 3,932,245 A | * 1/1976 | Erb et al. | ...................... 156/79 |
| 4,116,892 A | 9/1978 | Schwarz | ...................... 521/62 |
| 4,153,664 A | 5/1979 | Sabee | ...................... 264/289 |
| 4,153,751 A | 5/1979 | Schwarz | ...................... 428/304 |
| 4,289,832 A | 9/1981 | Schwarz | ...................... 428/542 |
| 4,753,840 A | 6/1988 | Van Gompel | ............... 428/171 |
| 5,035,941 A | 7/1991 | Blackburn | ................... 428/286 |
| 5,156,793 A | 10/1992 | Buell et al. | .............. 264/288.8 |
| 5,167,897 A | 12/1992 | Weber et al. | ............. 264/288.8 |
| 5,409,761 A | 4/1995 | Langley | ...................... 428/198 |
| 5,492,753 A | 2/1996 | Levy et al. | .................. 428/219 |
| 5,582,903 A | 12/1996 | Levy et al. | .................. 428/219 |
| 5,626,571 A | 5/1997 | Young et al. | ................ 604/370 |
| 5,628,097 A | 5/1997 | Benson et al. | ................. 28/165 |
| 5,650,214 A | 7/1997 | Anderson et al. | ............ 428/152 |
| 5,789,065 A | * 8/1998 | Haffner et al. | ............... 428/152 |
| 5,865,926 A | 2/1999 | Wu et al. | .................... 156/229 |
| 5,910,225 A | 6/1999 | McAmish et al. | .......... 156/229 |
| 5,914,084 A | 6/1999 | Benson et al. | .............. 264/284 |
| 6,013,151 A | 1/2000 | Wu et al. | .................... 156/229 |
| 6,114,263 A | 9/2000 | Benson et al. | .............. 442/394 |

FOREIGN PATENT DOCUMENTS

| | | |
|---|---|---|
| EP | 0 995 413 A1 | 4/2000 |
| EP | 0 995 414 A1 | 4/2000 |
| WO | WO 96/16562 | 6/1996 |
| WO | WO 96/31345 | 10/1996 |
| WO | WO 98/37266 | 8/1998 |
| WO | WO 98/51475 | 11/1998 |
| WO | WO 99/22930 | 5/1999 |
| WO | WO 99/32272 | 7/1999 |
| WO | WO 99/32698 | 7/1999 |
| WO | WO 99/37840 | 7/1999 |
| WO | WO 99/45871 | 9/1999 |
| WO | WO 99/62449 | 12/1999 |
| WO | WO 00/06377 | 2/2000 |

* cited by examiner

*Primary Examiner*—Allan R. Kuhns
(74) *Attorney, Agent, or Firm*—Caroline Wei-Berk; Ken K. Patel; Steven W. Miller

(57) ABSTRACT

A method is disclosed for modifying the physical characteristics of a web which involves passing the web between at least one pair of interengaged rolls to incrementally stretch the web, and then withdrawing the incrementally stretched web from between the rolls under tension. A web modified according to the disclosed method has desirable breathability and liquid impermeability, as well as extensibility and a soft, cloth-like textured surface. One embodiment of the present invention provides a breathable web comprising a microporous film exhibiting an MVTR of at least about 2000 g/m$^2$/24hr, a dynamic impact value of less than about 10 g/ m$^2$, a bubble pressure at least about 45 psi, and an air flow of at least about 2 liters/m$^2$/s.

15 Claims, 9 Drawing Sheets

METHOD OF MAKING A BREATHABLE AND LIQUID IMPERMEABLE WEB

This application is a continuation-in-part application of a provisional U.S. application serial no. 60/156,900, filed Sep. 30, 1999, in the name of Dobrin et al.

FIELD OF THE INVENTION

The present invention relates to an improved breathable web and an economical method for advantageously modifying the physical properties of a web for use as a component of a disposable absorbent article, and to disposable articles incorporating such modified webs.

BACKGROUND OF THE INVENTION

Disposable, wearable articles having an inner, body-facing, liquid pervious component, an intermediate, absorbent, liquid-retaining component and an outer, garment-facing, liquid-impervious component are well known. Articles of that type are commonly available in the form of disposable diapers, disposable underwear, pull-on diapers and training pants, incontinence pads, incontinence briefs, sanitary napkins, pantiliners, and the like. Such articles generally include a flexible, liquid-impervious outercover (i.e., backsheet) that is adapted to be positioned between an absorbent component of the article and the clothing of the wearer, to prevent wetting or soiling of the wearer's clothing when the article is in use.

In order to provide improved comfort to the wearer of disposable absorbent articles, certain components of the articles, such as a backsheet, in addition to providing imperviousness to liquids, desirably permit the passage therethrough of moisture vapor and also preferably air, to help maintain dryness and to reduce the humidity adjacent the wearer's body. An impervious polymeric film to which breathability has been imparted to allow air and moisture vapor transmission through the film is disclosed U.S. Pat. No. 3,156,342, entitled "Flexible Absorbent Sheet," which issued on Nov. 10, 1964, to G. A. Crowe, Jr.; U.S. Pat. No. 3,881,489, entitled "Breathable, Liquid Impervious Backsheet for Absorbent Devices," which issued on May 6, 1975 to Edward Wallace Hartwell, et al.; U.S. Pat. No. 3,989, 867, entitled "Absorbent Devices Having Porous Backsheet," which issued on Nov. 2, 1976, to James Bryant Sisson; U.S. Pat. No. 4,153,751, entitled "Process for Stretching an Impregnated Film of Material and The Microporous Product Produced Thereby," which issued on May 8, 1979, to Eckhard C. A. Schwarz; and U.S. Pat. No. 4,539,256, entitled "Microporous Sheet Material, Method of Making and Articles Made Therewith," which issued on Sep. 3, 1985, to Gene H. Shipman.

In addition to imperviousness to liquids, and pervious to moisture vapor and air, the backsheet also preferably includes a cloth-like outer surface, which provides a softer feel, and also a more appealing visual appearance, as compared with the outer surface of a smooth, flat plastic film. Two-ply backsheets that provide a desirable, more cloth-like appearance for such disposable, wearable articles are also known. In that regard, U.S. Pat. No. 5,151,092, entitled "Absorbent Article with Dynamic Elastic Waist Feature Having a Predisposed Resilient Flexural Hinge," which issued on Sep. 29, 1992, to Kenneth B. Buell, et al., discloses a disposable diaper backsheet formed either from a woven or a nonwoven material, a polymeric film, or a composite material in the form of a film-coated, nonwoven material. That patent also discloses the step of embossing of a plastic film backsheet to provide a more cloth-like appearance to a plastic film.

Also known to those skilled in the art are methods for imparting extensibility to an otherwise substantially inelastic material, which may be employed as a backsheet. For example, the use of corrugating rolls to laterally or longitudinally stretch and to simultaneously provide a corrugated form to thin plastic films is disclosed in U.S. Pat. No. 4,116,892, entitled "Process for Stretching Incremental Portions of an Orientable Thermoplastic Substrate and Product Thereof," which issued on Sep. 26, 1978, to Eckhard C. A. Schwarz; U.S. Pat. No. 4,834,741, entitled "Diaper With Waistband Elastic," which issued on May 30, 1989, to Reinhardt N. Sabee; U.S. Pat. No. 5,156,793, entitled "Method for Incrementally Stretching Zero Strain Stretch Laminate Sheet In A Non-Uniform manner To Impart A Varying Degree Of Elasticity Thereto," which issued on Oct. 20, 1992, to Kenneth B. Buell et al.; U.S. Pat. No. 5,167,897, entitled "Method for Incrementally Stretching A Zero Strain Stretch Laminate Sheet To Impart Elasticity Thereto," which issued on Dec. 1, 1992 to Gerald M. Webber et al.; and U.S. Pat. No. 5,422,172, entitled "Elastic Laminated Sheet Of An Incrementally Stretched Nonwoven Fibrous Sheet and Elastomeric Film and Method," which issued on Jun. 6, 1995, to Pai-Chuan Wu. The corrugating rolls disclosed in each of those patents are employed in carrying out a process sometimes referred to as "ring-rolling," to locally stretch and form corrugations in the material, in order to impart a greater degree of stretchability to selected portions of a sheet or web that may serve as a backsheet for disposable absorbent articles. Such backsheets can include both a polymeric film and an overlying and contacting layer of nonwoven, fibrous material.

Although there have been significant product improvements in recent years that have resulted in improved functioning and increased consumer acceptance of disposable absorbent articles, it is still desirable to provide an improved material having optimal physical properties relating to permeability to water vapor and air, and impermeability to liquid. Additionally, the improved material should desirably have the optimal properties that are particularly useful in an absorbent article, such as good liquid impact value, and air flow rate. It is further desirable that the improved material has a soft, cloth-like outer surface and extensibility useful for comfort and fit provided by absorbent articles containing such a material.

It would also be advantageous to provide an economical method for modifying a pre-formed web or laminate to have desirable properties which can be used as a structural component or an extensible component of a disposable absorbent article.

SUMMARY OF THE INVENTION

The present invention provides an improved method of modifying the physical characteristics of a web at high web speed. The precursor web is passed between at least one pair of interengaged rolls to incrementally stretch the web, then the incrementally stretched web is withdrawn from between the rollers under tension. An engineering strain rate from about 50 $s^{-1}$ to about 1650 $s^{-1}$ is found to be effective in achieving a modified web with desired properties. The method of the present invention is applicable at a temperature from ambient to about 120° C., and a web speed from about 30 m/min to about 365 m/min.

The modified web has a microporous structure containing few large pores and capillaries. Thus, the resultant microporous web is breathable to air or vapor, but acts as a liquid barrier under the impact pressure commonly imposed by the wearer of an absorbent article. Particularly, the microporous web has good breathability (as manifested in moisture vapor transmission rate and air flow rate) while maintaining satisfactorily low leakage under impact pressure. Additionally, the modified web can have a soft, cloth-like surface and extensibility for improved fit and wearer comfort.

The webs may be films, nonwovens, or composites of films and nonwoven webs, such as laminates. Typically, the web is made of thermoplastic materials which may be a blend of thermoplastic polymers and pore-forming agents such as incompatible organic materials or inorganic particulate materials. In the incremental stretching process of the present invention, the pore-forming agent is activated and the resultant web has pores and channels (i.e., interconnected pores) through the thickness of its structure, which is generally referred to as a "microporous" web.

The breathable and liquid impermeable web of the present invention comprises at least a microporous film and has an MVTR (moisture vapor transmission rate) of at least about 2000 g/m$^2$/24 hr, a dynamic impact value of less than about 10 g/ m$^2$, a bubble pressure at least about 45 psi, and optionally, an air flow of at least about 2 liters/m$^2$/s.

DETAILED DESCRIPTION OF THE INVENTION

Figure 1:
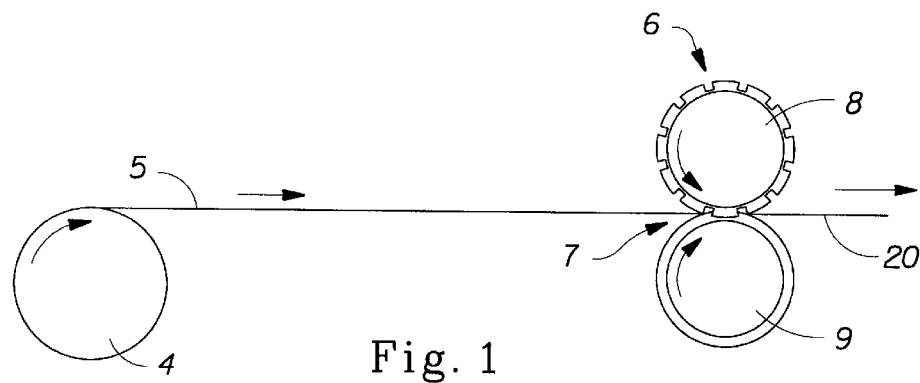
FIG. 1 is a schematic illustration of an exemplary process and apparatus for modifying a web and imparting breathability to a web in accordance with the present invention.

The present invention is directed to the modification of the physical properties, and if desired the dimensions, of materials intended for use in disposable absorbent articles. After modification, the material can, if desired, be joined with other materials for incorporation as functional and structural elements of disposable absorbent articles. Examples of such materials include precursor films that can be made to be liquid impervious and breathable, elastomeric films, nonwoven webs, foams, woven webs and the like. Although disclosed herein in the context of use with disposable articles, it will be apparent to those skilled in the art that such modified materials also can be employed in other structures intended for other uses, including wound dressing, medical drapes, surgical gowns, extensible fabrics and garments.

As used herein, the term "extensibility" refers to the degree to which any material can be stretched, either in the web movement direction or in the cross-web direction, when a tensile biasing force is applied to the material without catastrophic failure of the material. The elongation is expressed herein as a percent (%), and is based upon the original, unstretched length and the stretched length immediately before rupture or failure of the material.

As used herein, the term "extensible" refers to any material that upon application of a biasing force is stretchable, or that is elongatable by at least about 50% (i.e., having a stretched, biased length that is at least about 150% of its relaxed, unbiased length).

As used herein, the term "load to elongate" refers to the biasing force that must be applied to any material to elongate it to a given elongation, either in the web movement direction or in the cross-web direction, wherein the elongation is expressed as a percent (%), and is the ratio between the stretched length and the original, unstretched length.

As used herein the term "laminate" refers to a material that includes two or more webs of materials joined to each other to achieve a unitary structure. The webs can be joined to each other substantially continuously, at spaced-apart locations, or at intermittent points.

As used herein, the term "nonwoven" refers to a fibrous web or sheet that has a structure of individual fibers or threads that are interlaid, but not in any regular, repeating manner. Nonwoven sheets have in the past been formed by a variety of processes, such as meltblowing, spunbonding processes, and carded bonding, or combinations thereof.

As used herein, the term "thermoplastic" refers to a polymeric material which can be melted and resolidified with little or no change in physical properties (assuming a minimum of oxidative degradation).

As used herein, the term "precursor web" refers to a polymeric web prior to being modified such that micropores are provided in the web, particularly in the film component, to allow the web to have increased breathability while remaining substantially liquid impervious.

As used herein, the term "breathable film" refers to a film that is capable of permitting the passage therethrough of moisture vapor and also preferably air, but that does not permit the passage therethrough of liquids to an undesirable extent.

As used herein, the term "surface contour length" refers to a measurement along a topographic surface of a material in a specified direction.

MODIFICATION OF WEBS

FIG. 1, is a schematic illustration of an apparatus suitable for use in the method of the present invention for modifying the physical and performance properties, and if desired the size, of a web. The apparatus and method provide a physically modified web having improved physical properties and modified which may be used in disposable absorbent articles for improved performance and fit/comfort provided by the articles. Additionally, after being modified in the disclosed apparatus and after having acquired the desired physical properties hereinafter described, such modified webs are capable of being further processed, either alone or together with other materials, and without the modified web experiencing disintegration, rupture, or loss of integrity.

As used herein, the word "web" is intended to encompass continuous rolls and discrete sheets of the materials, though the web in a continuous form is more suitable for high-speed production purposes.

The web has a longitudinal axis that extends along the web movement or "machine" (MD) direction of the web, and a transverse axis that extends in the cross-web or "cross-machine" (CD) direction of the web.

Referring again to FIG. 1, web 5 is withdrawn from supply roll 4 and travels in the direction indicated by the arrow. Alternatively, web 5 is formed directly off an extruder equipped with a film die, and optionally a set of tension or take-up rolls between the extruder and forming station 6. Web 5 is fed to the nip 7 formed by a pair of opposed forming rolls 8 and 9 that together define a first forming station 6. The structure and relative positions of forming rolls 8, 9 are shown in an enlarged perspective view in FIG. 2. As shown, rolls 8 and 9 are carried on respective rotatable shafts 21, 23, having their axes of rotation disposed in parallel relationship. Each of rolls 8 and 9 includes a plurality of axially-spaced, side-by-side, circumferentially-extending, equally-configured teeth 22 that can be in the form of thin fins of substantially rectangular cross section, or they can have a triangular or an inverted V-shape when viewed in cross section. If they are triangular, the vertices of teeth 22 are outermost. In any event, the outermost tips of the teeth are preferably rounded, as shown in greater detail in FIGS. 3 and 4, to avoid cuts or tears in the materials, such as web 5, that pass between the rolls.

The spaces between adjacent teeth 22 define recessed, circumferentially-extending, equally configured grooves 24. The grooves can be of substantially rectangular cross section when the teeth are of substantially rectangular cross section, and they can be of inverted triangular cross section when the teeth are of triangular cross section. Thus, each of forming rolls 8 and 9 includes a plurality of spaced teeth 22 and alternating grooves 24 between each pair of adjacent teeth. The teeth and the grooves need not each be of the same width, however, and preferably the grooves have a larger width than that of the teeth, to permit the material that passes between the interengaged rolls to be received within the respective grooves and to be locally stretched, as will be explained hereinafter.

Figure 3:
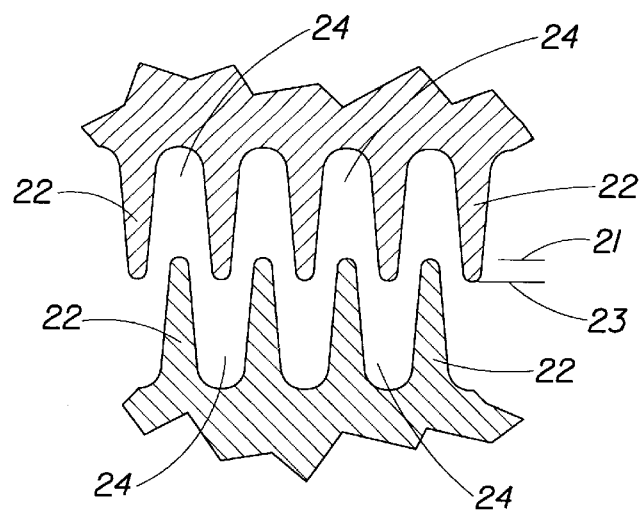
FIG. 3 is an enlarged, fragmentary, cross-sectional view showing the interengagement of respective teeth and grooves of the forming rolls shown in FIG. 2.

FIG. 3 is an enlarged, fragmentary, cross-sectional view showing the interengagement of teeth 22 and grooves 24 of the respective rolls. As shown, generally triangular teeth 22 of one roll extend partially into generally triangular grooves 24 of the opposed roll, so that imaginary lines 21 and 23 interconnecting the rounded outer tips of teeth 22 of rolls 8 and 9, respectively, lie radially inwardly of the rounded outer tips of teeth 22 of the opposed roll. The respective axes of rotation of rolls 8 and 9 so spaced from each other that there is a predetermined space or gap between the opposed sidewalls of the interengaged teeth and grooves of the respective rolls.

Figure 4:
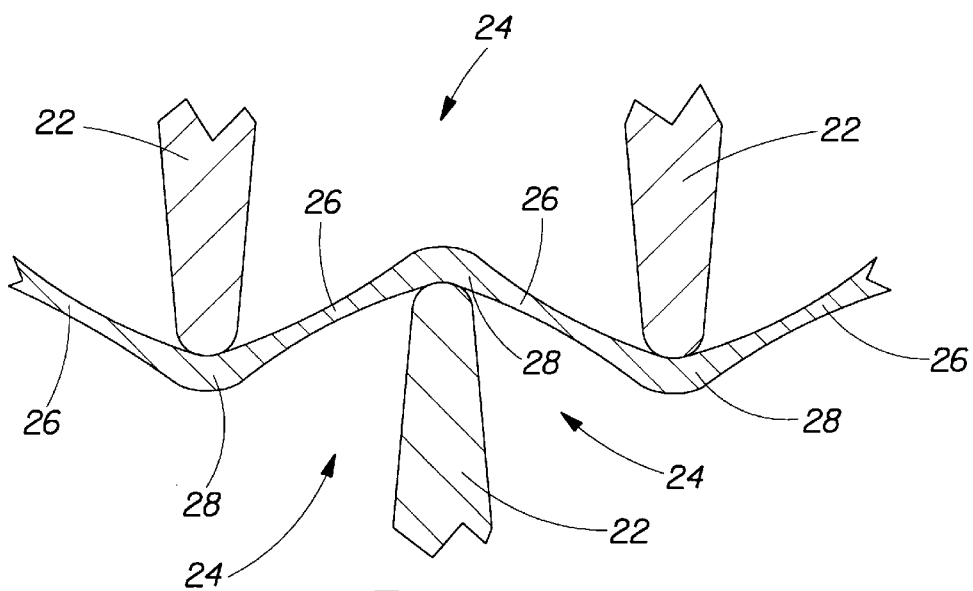
FIG. 4 is a further enlarged, fragmentary, cross-sectional view showing the tip portions of the interengaged forming roll teeth with a web of material positioned between the rolls and spanning and in contact with the tips of adjacent teeth.

FIG. 4 is an even further enlarged view of several interengaged teeth 22 and grooves 24 with a web of material being modified therebetween. As shown, a portion of web 20, which is the modified material of the precursor web 5 of FIG. 1, is received between the interengaged teeth and grooves of the respective rolls. The interengagement of the teeth and grooves of the rolls causes laterally spaced portions of web 20 to be pressed by teeth 22 into opposed grooves 24. In the course of passing between the forming rolls, the forces of teeth 22 pressing web 20 into opposed grooves 24 impose within web 20 tensile stresses that act in the cross-web direction. The tensile stresses cause intermediate web sections 26 that lie between and that span the spaces between the tips 28 of adjacent teeth 22 to stretch or extend in a cross-web direction, which results in a localized reduction of the web thickness at each of intermediate web sections 26.

In one embodiment, there is a substantially uniform distribution of local strain over the span between adjacent teeth. The portions of web 20 that lie between the adjacent teeth are locally stretched while the portions of the web that are in contact the tips of the teeth typically do not undergo a similar degree of extension. Not intending to be bound by theory, it is believed that the frictional forces exist between the surfaces at the rounded outer ends (i.e., tips) of teeth 22 and the adjacent surfaces 28 of web 20 that are in contact therewith. The frictional forces reduce the sliding movement of those portions of the web surfaces relative to the tooth tip surfaces. Consequently, the thickness of web portion 28 that are in contact with the tooth tips reduces only slightly, as compared with the web thickness reductions that occur at intermediate web portion 26.

Figure 5:
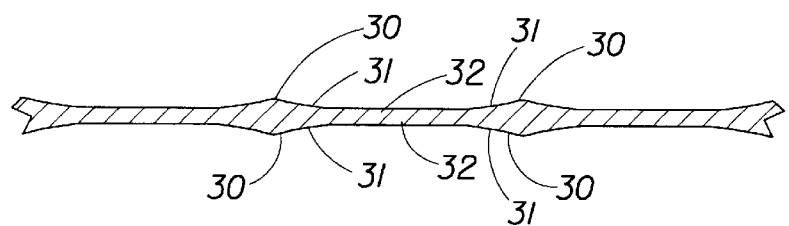
FIG. 5 is an enlarged, fragmentary, cross-sectional view taken along the cross-web direction of a web of material that has passed through a pair of forming rolls such as those shown in FIG. 2.

However, in a typical process according to the present invention, there is a nonuniform distribution of the local strains over the span between adjacent teeth. FIG. 5 illustrates the modified web having a drawn portion 32 which has been fully drawn (i.e., drawn to the natural draw ratio of the material), an unstretched portion 30 and an intermediate portion 31. When material is substantially fully drawn in web portion 32, no further deformation takes place and no more open areas are being formed. Thus, the micropores and capillaries are "stabilized" or "fixed". The area where the web material are being stretched are primarily in the intermediate portion 31. In the local (i.e., between adjacent web portions 30, 31 and 32) stretching process, the web material in the unstretched portion 30 are being incorporated into the intermediate portion 31 where the deformation takes place. The intermediate portion 31 is typically referred to as the "neck" region. As used herein, the term "neck" refers to the constriction in at least one dimension by applying a tension force in a direction perpendicular to the desired direction of constriction (which is sometimes called a "neck down").

The action of pressing of portions of web 20 into the respective grooves 24 by teeth 22 therefore causes a non-uniform reduction of the thickness of web 20 to take place in the cross-web direction of the web. Accordingly, web 20 undergoes a greater reduction in thickness in the cross-web portions of the web that extend between and that span adjacent teeth 22 than it undergoes at those cross-web portions of the web that are in contact with the surfaces at the outer ends of teeth 22. Thus, by virtue of passing through the interengaged rolls and being locally laterally stretched at spaced intervals between adjacent teeth, the upper and lower surfaces of the web after it passes from between the opposed rolls define modulating surfaces that are the mirror images of each other when the web is viewed in cross section in the cross-web direction, as shown in FIG. 5. Modulating upper and lower surfaces of the web include alternating peaks 30 and valleys 32, which define alternating heavy and light basis weight regions. The light basis weight regions are found at the positions of the web wherein the web material has been locally laterally stretched. The localized stretching of the web in the cross-web direction results in a wider (as manifested in the increase in the surface contour length) modified web that has a plurality of spaced, longitudinally-extending, localized areas of reduced web thickness. Additional cross-web stretching of the exiting, formed web can be effected by passing the modified web between so-called Mount Hope rolls, tentering frames, angled idlers, angled nips, and the like (not shown), each of which is known to those skilled in the art.

Because of the localized cross-web stretching of web 5 that has taken place, with the consequent increase in web width, the modified web 20 that exits from the forming rolls at first forming station 6 has a lower basis weight than that of the entering precursor web 5, provided the exiting material remains in a substantially flat, laterally extended state. The laterally-stretched web as it exits from between the forming rolls may contract laterally to its original width. When the web is placed under some tension in the web movement direction, the exiting, modified web may have the same basis weight as it had in its entering condition. If the exiting modified web is subjected to a sufficiently high web movement direction tension, the exiting modified web can be made to contract to a smaller width than its original width, in which case the web will have a greater basis weight than its original basis weight. On the other hand, if the web is subjected to sufficient additional cross-web stretching by passing the modified web between so-called Mount Hope rolls, tentering frames, angled idlers, angled nips, or the like as described above, the exiting, modified web will have less than its original basis weight. Thus, by selecting a suitable forming roll tooth and groove configuration, by selecting a suitable web movement direction tension level, and by selecting whether or not to subject the web to additional cross-web stretching, the resulting modified web can have a web width that can range from about 25% to about 300% of the unmodified, precursor web width and a basis weight that is less than, equal to, or greater than the unmodified, precursor web's original basis weight.

Teeth 22 and grooves 24 can be generally triangular in cross section, as shown in FIG. 3, and preferably each of teeth 22 is of the same size so that each of the opposed teeth and grooves on respective forming rolls 8, 9 interengage with each other along the entire axial lengths of each of the rolls. In one embodiment, teeth having a peak-to-peak pitch of the order of about 0.030 to 0.100 inches, having sidewalls disposed at an included angle of the order of about 9° to 12°, and having a tip-to-base tooth height and groove depth of the order of about 0.060 to 0.300 inches can be employed in carrying out the present invention. As will be appreciated by those skilled in the art, the sizes of the respective teeth and grooves can be varied within a wide range and would still be effective to carry out the present invention. In that regard, additional structural details of suitable forming rolls are provided in U.S. Pat. No. 5,156,793, entitled "Method for Incrementally Stretching Zero Strain Stretch Laminate Sheet in a Non-Uniform Manner to Impart a Varying Degree of Elasticity Thereto," which issued on Oct. 20, 1992, to Kenneth B. Buell et al.; in U.S. Pat. No. 5,167,897 entitled "Method for Incrementally Stretching a Zero Strain Stretch Laminate Sheet to Impart Elasticity Thereto," which issued on Dec. 1, 1992, to Gerald M. Webber et al.; and in U.S. Pat. No. 5,518,801, entitled "Sheet Materials Exhibiting Elastic-Like Behavior," which issued on May 21, 1996, to Charles W. Chappell et al., the disclosures of each of which patents are hereby incorporated by reference herein.

If the web is expanded only in the X-Y plane, there will be a substantial decrease in the basis weight of the modified web, which serves to reduce the cost of any components of which the modified web is a part. Preferably, the width of the modified web of the present invention is about 100% greater than the original width of the unmodified, precursor web. On the other hand, if the web movement direction (MD) tension on the modified web as it exits the forming rolls is sufficiently high, the modified web will have a width that is less than its original width, and a greater basis weight than that of the unmodified, precursor web.

Figure 6:
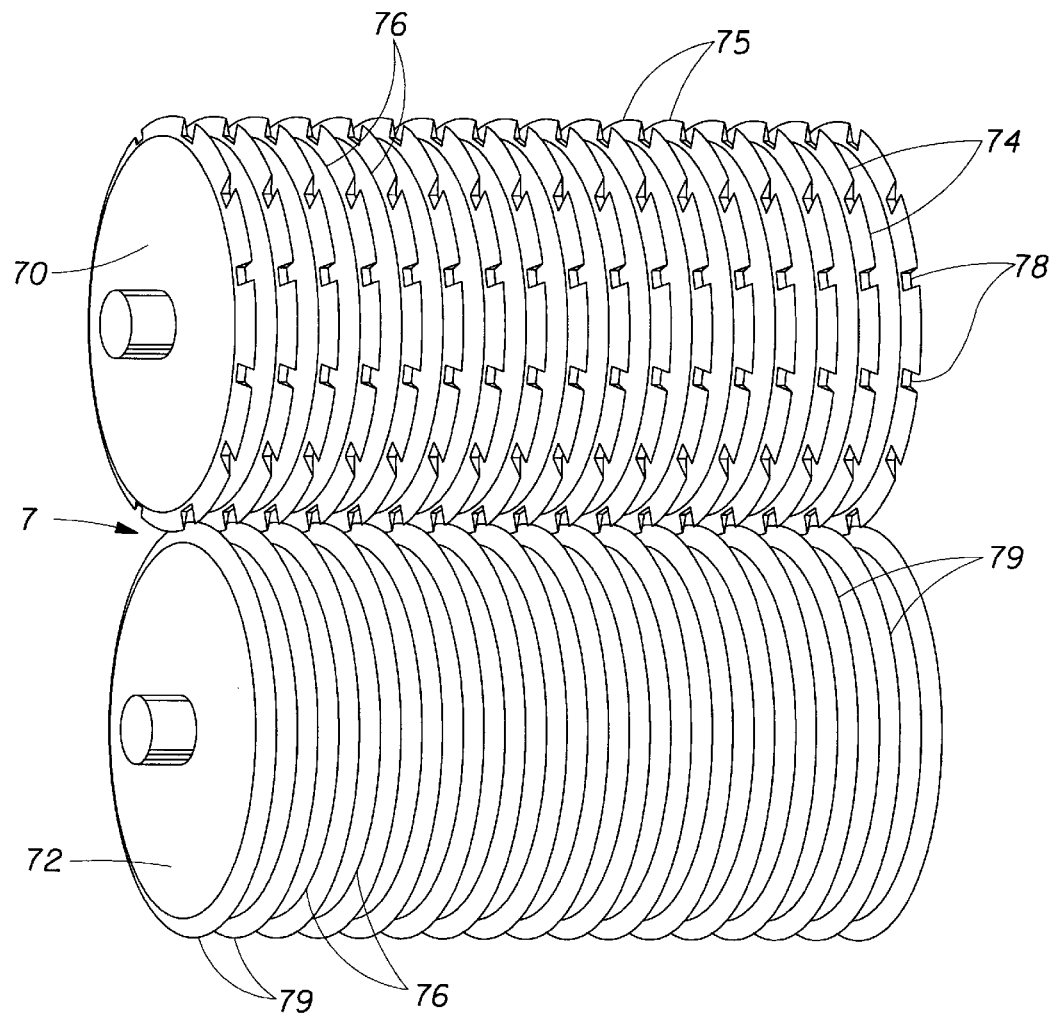
FIG. 6 is a fragmentary perspective view of a pair of closely-spaced forming rolls having tooth and groove configuration on the surface wherein one roll has notched teeth and the other roll has unnotched teeth.

FIG. 6 shows another configuration of opposed forming rolls, which can be used to expand portions of the web in the web thickness dimension, that is, by expanding portions of the web out of the X-Y plane into the Z-direction. As shown in FIG. 1, an unmodified web 5 is fed from a supply roll 4 into the nip 7 of opposed forming rolls 70 and 72 which define forming station 6. Roll 70 includes a plurality of circumferentially-extending, axially-spaced circumferential teeth 75. However, unlike continuous circumferential teeth 22 of forming roll 8 shown in FIG. 2, circumferential teeth 75 of roll 70 include a plurality of circumferentially-spaced ridges 74, and intervening circumferentially-spaced notched regions 78 that define recessed, open regions on teeth 75. As shown in FIG. 6, notches 78 on respective axially adjacent circumferential teeth 75 are aligned laterally to define a plurality of circumferentially-spaced groups of notched regions 78 about the periphery of roll 70. The respective laterally-extending groups of notched regions each extend parallel to the axis of roll 70.

Figure 2:
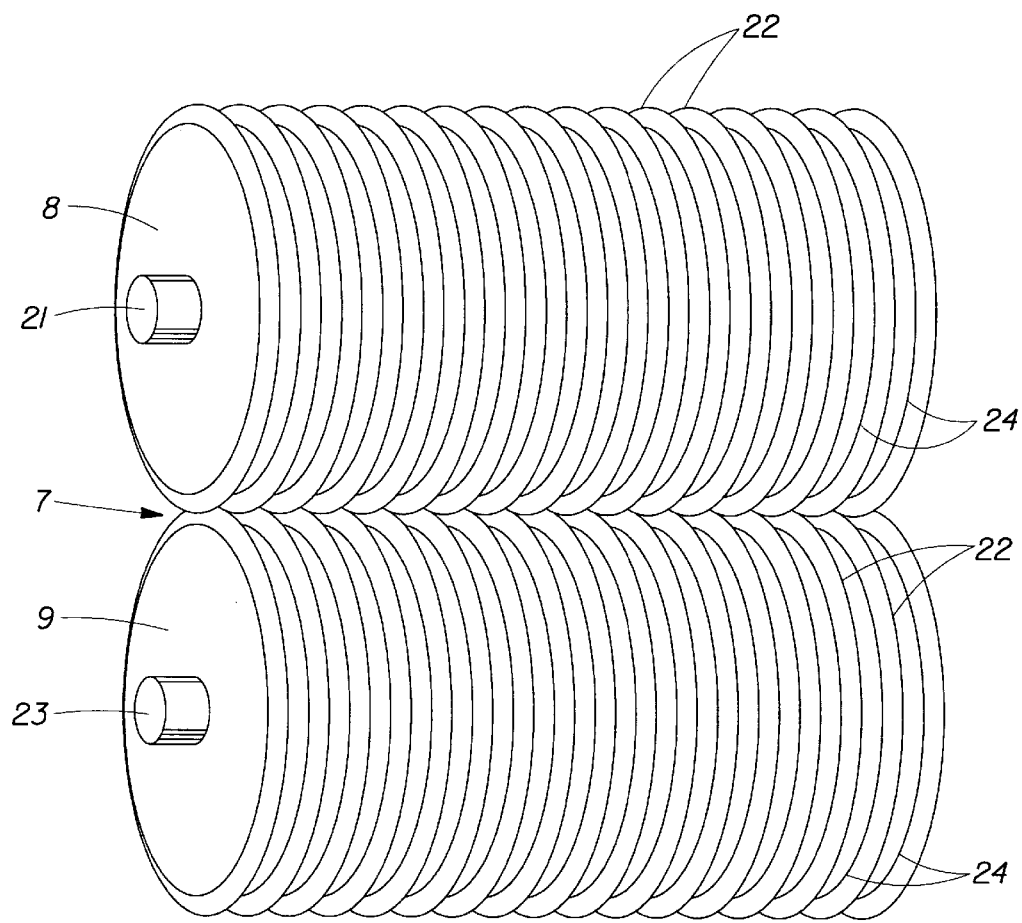
FIG. 2 is a fragmentary perspective view of a pair of closely-spaced forming rolls each having alternating and interengaging peripheral teeth and grooves.

Roll 72 is similar in overall construction to forming rolls 8 and 9 as shown in FIG. 2 in that roll 72 includes a plurality of circumferentially-extending, axially-spaced teeth 79 that extend in continuous, uninterrupted form about the circumference of the roll. Teeth 79 of roll 72 intermesh with teeth 75 of roll 70. But the portion of the web that passes between the notched regions 78 of roll 70 and the teeth 79 of roll 72 will be unformed, i.e., the web will not be deformed or stretched in that area and will remain substantially planar, while the portions of the web passing between ridges 74 of roll 70 and the teeth 79 of roll 72 will be deformed or stretched beyond the elastic limit of the web, resulting in a plurality of raised, rib-like elements. The raised, rib-like elements on the modified web provides a cloth-like texture, which improves the comfort and feel of the absorbent article containing such cloth-like, texturized web.

Figure 7:
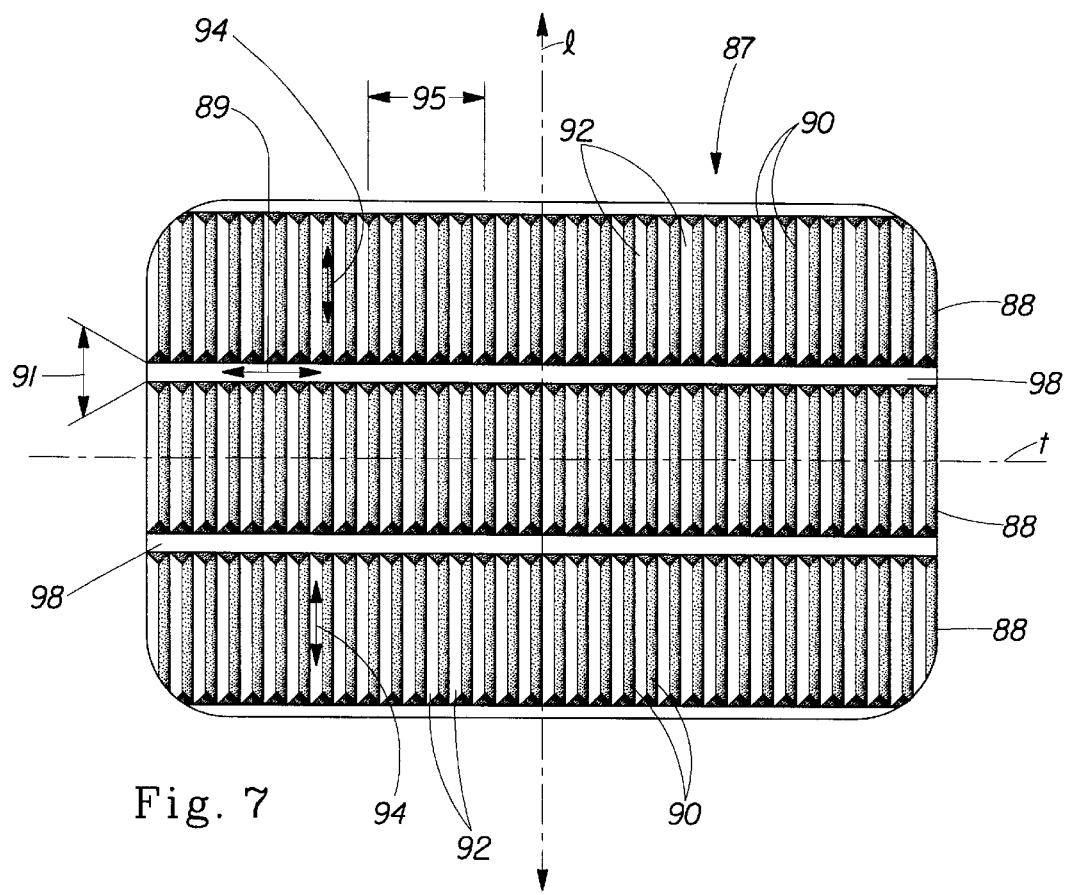
FIG. 7 is a top plan view of web material after it has passed between forming rolls having the teeth structure as shown in FIG. 6.
Figure 8:
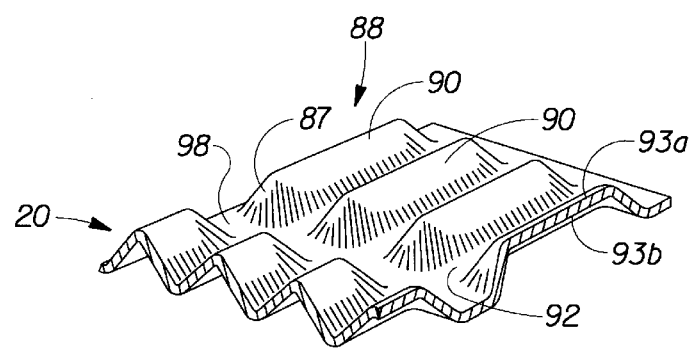
FIG. 8 is an enlarged fragmentary perspective view of a portion of the web shown in FIG. 7.

The forming rolls suitable for use herein to provide z-direction expansion in the modified web may have various tooth and groove configurations on the surface of the forming rolls. Typically, the teeth are spaced, circumferentially extending ridges (FIG. 2). The teeth may have circumferentially spaced notches in the ridges, producing spaced, rectangular arrays of raised ribs in the z-direction in the resulting modified web (FIGS. 7 and 8). More detailed descriptions and illustrations of the texturizing/forming rolls can be found in U.S. Pat. No. 5,518,801, issued May 21, 1996 to Chappell et al.; U.S. Pat. No. 5,650,214, issued on Jul. 22, 1997 to B. J. Anderson et al.; the disclosures of which are hereby incorporated by reference.

Referring now to FIGS. 7 and 8, there is shown a portion of a modified web 20 which has passed between a pair of opposed, interengaged forming rolls 70 and 72 having the tooth configurations shown in FIG. 6. Web 20 has two centerlines, a longitudinal centerline, which is also referred to hereinafter as an axis, line, or direction "l" and a transverse or lateral centerline, which is also referred to hereinafter as an axis, line, or direction "t". The transverse centerline "t" is generally perpendicular to the longitudinal centerline "l".

Web 20 includes a network of distinct regions. The network includes at least a first region 98, a second region 92, and a transitional region 87, which is at the interface between the first region 98 and the second region 88. Web 20 also has a first surface 93a and an apposite-facing second surface 93b. In the embodiment shown in FIGS. 7 and 8, web 20 includes a plurality of substantially flat, longitudinally spaced first regions 98 and a plurality of alternating second regions 88.

First regions 98 have a first, transversely-extending axis 89 and a second, longitudinally-extending axis 91, wherein the first axis 89 is preferably longer than the second axis 91. The first axis 89 of the first region 98 is substantially parallel to the transverse axis of web 20, while the second axis 91 is substantially parallel to the longitudinal axis of the web.

Second regions 88 have a first, transversely-extending axis 95 and a second, longitudinally-extending axis 94. The first axis 95 is substantially parallel to the transverse axis of the web, while the second axis 94 is substantially parallel to the longitudinal axis of the web. In the preferred embodiment of FIGS. 7 and 8, the first regions 98 and the second regions 88 are substantially linear, each extending continuously in a direction substantially parallel to the longitudinal axis of the web.

In the embodiment shown in FIGS. 7 and 8, first regions 98 are substantially planar. That is, the material within first regions 98 is substantially flat and is in substantially the same condition after the modification step undergone by web 20 by passage between interengaged rolls 70 and 72 shown in FIG. 6 as it was in before the web was passed between the forming rolls.

Second regions 88 include a plurality of raised, rib-like elements 90 that have a first or major axis 94 that is substantially parallel to the longitudinal axis of the web 20, and a second or minor axis 95 that is substantially parallel to the transverse axis of web 20. The dimension of rib-like elements 90 along first axis 94 is at least equal to, and preferably longer than, the dimension along second axis 95. Preferably, the ratio of the dimension of rib-like elements 90 along first axis 94 to the dimension along second axis 95 is at least 1:1, and more preferably at least 2:1 or greater. Further, rib-like elements 90 in second region 92 are adjacent one another and are separated from each other by an unformed area 98 having a width in the direction perpendicular to the major axis 94 of the rib-like elements. The dimensions of the rib-like elements can also be varied, if desired. A more detailed description of a web having first and second regions as shown in FIGS. 7 and 8 is provided in U.S. Pat. No. 5,518,801, the disclosure of which has already been incorporated herein by reference.

Figure 12:
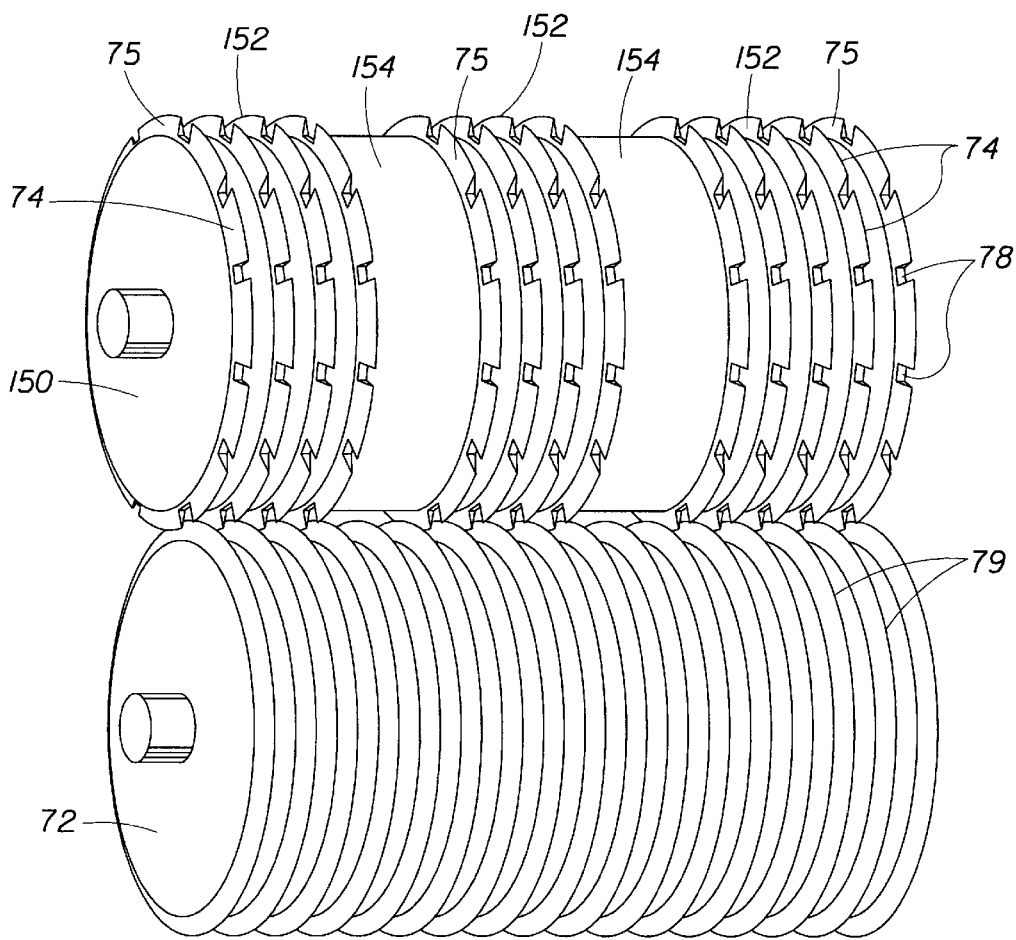
FIG. 12 is an enlarged, fragmentary perspective view of another set of forming rolls wherein the upper roll has interrupted teeth and groove configuration having notched teeth, and the lower roll has uninterrupted teeth.

Other arrangements of the teeth and grooves on the forming rolls known to those skilled in the art are also contemplated by the present invention. For example, the teeth may be arrangement in groups of rectangular arrays, wherein each group has several teeth and the respective groups of teeth are separated by an intervening gap that is devoid of teeth (FIG. 12). Additionally, the forming rolls may have decorative shapes, either as protruding teeth or as recessing grooves, on the roll surface. Nonlimiting examples of the decorative shapes include geometric shapes, animal shapes, floral or botanical shapes, cartoon figures.

Figure 10:
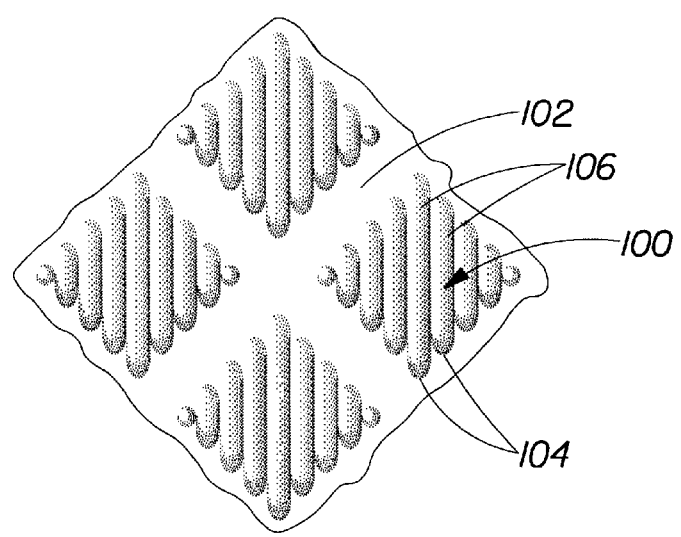
FIG. 10 is an enlarged fragmentary view of a portion of the modified web surface after the web has passed between a set of forming rolls having alternating teeth and grooves that define a diamond-like pattern.

In addition to the surface patterns illustrated in FIGS. 7 and 8 in the form of ridges and grooves, all of substantially equal lengths to define generally rectangular areas of deformation, the desired stretching or thinning of a web can, if desired, be effected by other forming roll tooth and groove configurations that can cause localized stretching of the material. For example, as shown in FIG. 10, instead of spaced rectangular arrays of ridges and grooves the deformation pattern can be in the form of ridges and grooves defining an array of spaced, diamond-shaped elements 100 with intervening undeformed areas 102. Each such diamond-shaped element is defined by alternating rib-like elements 106 and intervening grooves 104. Examples of methods and apparatus for formation of such diamond-shaped elements are disclosed in U.S. Pat. No. 5,650,214, entitled, "Sheet Materials Exhibiting Elastic-Like Behavior and Soft, Cloth-Like Texture", which issued on Jul. 22, 1997, to Barry J. Anderson, et al., the disclosure of which is incorporated herein by reference.

Figure 11:
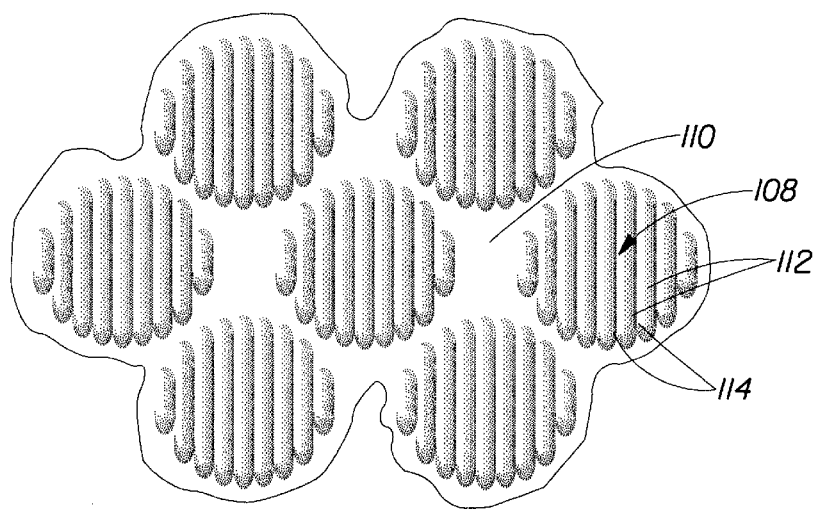
FIG. 11 is a fragmentary perspective view of a modified web surface, illustrating another forming roll tooth and groove pattern.

As shown in FIG. 11, the deformation pattern can also be in the form of ridges and grooves that together define an array of spaced, circularly-shaped elements 108. Each such circular element can be defined by varying-length rib-like elements 114 and intervening grooves 112. Between respective circularly-shaped elements 108 are unformed intervening areas 110. As will be apparent to those skilled in the art, other deformation patterns can also be employed, if desired, such as those illustrated and described in U.S. Pat. No. 5,518,801, the disclosure of which was earlier incorporated herein by reference.

Another set of forming rolls, having a different arrangement of the peripheral teeth and grooves and that can be utilized in the practice of the present invention, is shown in FIG. 12. Forming roll 150 is similar to forming roll 70 shown in FIG. 6 except that the circumferentially-extending teeth 75 are provided in respective groups 152, each group containing several teeth 75. Each of groups 152 of teeth 75 is spaced from an adjacent group of teeth in the axial direction of the roll, and the respective groups of teeth are separated by an intervening gap 154 that is devoid of teeth. Forming roll 72 of FIG. 12 has the same configuration as forming roll 72 of FIG. 6.

Because of the general structural similarity of the teeth and grooves on the several forming rolls shown in FIGS. 2, 6, and 12, the same reference numerals have been applied to corresponding parts of the rolls shown in FIGS. 2, 6, and 12.

In addition to modifying the dimensions of a web by extending the web, for example, in the X-Y plane to lower its basis weight, and by adding loft to the web in the Z direction, the present invention is also directed to modifying the physical properties of the web in a beneficial way. As used herein the term "physical properties" refers to the performance characteristics of the web, including the strength of the web when subjected to a tensile force, its extensibility when subjected to a tensile force, and the force needed to elongate the web to a point short of tearing or rupture of the web material. The term "physical property" also includes web characteristics that relate to the performance of the web used as a component of an absorbent article, such as moisture vapor transmission rate (MVTR), dynamic fluid impact value, bubble pressure and air flow rate. Those desirable physical property modifications can be achieved by passing the web through at least one pair of the interengaged forming rolls that have been described herein, and optionally, applying some tension in the web-movement direction. Additionally, the present invention also encompasses successive modifications of the web by passing the web through successive sets of forming rolls, tensioning and, if desired, additional cross-web direction stretching. For example, a first set of forming rolls can serve to increase the extensibility of the web without causing shredding or tearing of the web, and a second set of forming rolls can serve to expand the web in the X-Y plane.

When the web materials, such as nonwoven webs, films, or laminates thereof, are incorporated in a disposable absorbent article, it is typical that the cross-web (CD) strength of the modified web of the present invention be substantially lower than that of an unmodified web. It is also typical that the cross-web extensibility of a modified web of the present invention is substantially higher than that of an unmodified web. It is further typical that the load to elongate of a modified web of the present invention is substantially lower than the typical values attainable from commercially available, nonwoven webs. A modified web of the present invention exhibits (1) a load to achieve 10% cross-web elongation of from about 5% to about 100% of the corresponding cross-web elongation load of the unmodified web; (2) a load to achieve 30% cross-web elongation of from about 5% to about 100% of the corresponding cross-web elongation load of the unmodified web; and (3) a cross-web extensibility of from about 105% to about 200% of the cross-web extensibility of the unmodified web. Such an extensible web more easily be conforms with and adapts to the contours of the body of a wearer of a disposable article, both during application of the article to the body as well as while being worn and being subjected to loads as a result of body movements of the wearer. The improved fit and adaptability to changing wearing conditions leads to greater wearer comfort.

Suitable nonwoven webs are typically prepared from fibers of thermoplastic polymers such as polyolefins, polyesters, polyamides, cellulose derivatives such as rayon, and copolymers and mixtures thereof. Preferably, the nonwoven webs are made of polyolefins such as polyethylene, polypropylene, polybutylene, and their copolymers. The fibers may be of a single polymer or of a blend of polymers. The nonwoven web may be made of fibers having different compositions. Bi-component fibers made from two different polymers or blends, arranged in a sheath-core, or side-by-side configuration, are also suitable for use herein. Also useful herein are bi-component fibers having a sheath-core structure with a lower melting polymer or blend in the sheath. For example, the fiber may have a sheath of polyethylene and a core of polypropylene and copolymer, or polyester and copolymers. The nonwoven web may be made by processes known to those skilled in the art, including carding, meltblowing, spunbonding and combinations thereof Modified web materials may be incorporated into a disposable absorbent article, including nonwoven webs, polymeric films, and laminates or other composite structures thereof. For example, a modified web can be utilized as a component of a composite, breathable backsheet, one that is liquid impervious but that is pervious to gases and moisture vapor and that preferably has at least one soft, cloth-like outer surface.

MODIFICATION OF A WEB CONTAINING PORE-FORMING AGENTS

When an unmodified web is a film containing poreforming agents or incompatible fillers, the modification process and apparatus disclosed herein advantageously impart breathability to the modified film while imparting minimal adverse effect on the leakage performance of the modified web. Breathability can be imparted to a polymeric film, while maintaining its imperviousness to liquids, by forming micropores in the film. The desired micropores should be sufficiently small in order to prevent the passage therethrough of liquids, but they are large enough for the passage therethrough of air and moisture vapor. Micropores can be formed directly in an otherwise solid film in several ways, including perforating the film as disclosed in U.S. Pat. No. 3,881,489, entitled "Breathable, Liquid Impervious Backsheet for Absorbent Devices", which issued on May 6, 1975, to Edward Wallace Hartwell. Perforations can be provided by mechanically puncturing the film, but that technique requires close tolerance control over the puncturing elements of the apparatus, which over time might provide micropores of increasingly greater size as a result of mechanical wear of the puncturing elements. Larger pores could allow the undesired passage of liquids through such films.

Another way to enable the formation of micropores in an otherwise impervious film involves substantially uniformly dispersing pore forming agents within a thermoplastic polymer matrix. The dispersion of the pore forming agents can be effected by a mixing step, and the resulting mixture can be formed into a thin film by extruding, casting, or blowing techniques that are known to those skilled in the art. The pore forming agents include incompatible organic materials and inorganic particulates. As used herein, the term "incompatible" means organic or inorganic materials that are incapable of being dissolved in the polymer, so that those materials retain their original form and composition and remain separate and distinct from, but are surrounded by, the polymer matrix. Formation of the micropores is effected after the film has been modified, by locally stretching the precursor film in a manner that is described in detail hereinafter.

Nonlimiting examples of incompatible organic materials include polystyrenes, polycarbonates, polyacrylates, fluorocarbon polymers or low melting resins, polyterephthalates, and copolymers and mixtures thereof. The preferred incompatible organic materials as pore forming agents are polystryene and copolymers. Another exemplary organic material that can be used as a pore forming agent is mineral oil, as disclosed in U.S. Pat. No. 4,609,584, entitled "Absorptive Devices," which issued on Sep. 2, 1986, to Cutler et al., the disclosure of which is incorporated herein by reference.

Nonlimiting examples of inorganic materials that can be used as pore forming agents include calcium carbonate, titanium dioxide, clays, silicas, zeolites, kaolin, mica, carbon, and mixtures thereof. Calcium carbonate is a preferred inorganic particulate material because it is cheap and commercially available. Preferably, the inorganic particle is supplied in particulate form, having a particle size ranging from about 1 to about 5 microns, and it can constitute from about 5 to about 70 percent by weight of the polymer-particulate mixture. The inorganic particle can optionally be coated with a fatty acid ester to enable higher loadings of the inorganic particle to be included in the polymer-inorganic mixture. Suitable other inorganic particles are disclosed in U.S. Pat. No. 4,472,328, entitled "Process for Producing Porous Film or Sheet," which issued on Sep. 18, 1984, to Sugimoto et al., and in U.S. Pat. No. 4,777,073, entitled "Breathable Films Prepared From Melt Embossed Polyolefin/Filler Precursor Films," which issued on Oct. 11, 1988, to Sheth, the disclosures of both patents are incorporated herein by reference.

Typically, the pore forming agents comprises at least about 5 wt % of the polymer, preferably from about 10 wt % to about 70 wt %, more preferably from about 20 wt % to about 60 wt %, and most preferably from about 30 wt % to about 50 wt %. The average size of the pore forming agents should be less than about 50 microns, preferably less than about 10 microns and more preferably less than 5 microns. The size distribution of the pore forming agents should be such that less than 10% of the agents have a size greater than 50 microns.

Mixing of the pore forming agents and the thermoplastic polymer can be effected in any suitable mixing device, such as a mixing extruder, to obtain a substantially uniform mixture of the components. Preferably, the pore forming agents are substantially uniformly dispersed throughout the polymeric matrix material. A flexible precursor film having a thickness of the order of from abut 0.3 mils to about 5 mils can be formed from such a mixture using known film forming equipment and techniques.

Suitable polymers for use herein in a film of the present invention include thermoplastic polyolefins, such as polyethylene, polypropylene, polybutylene, and their copolymers and mixtures thereof. Various types of polyethylenes such as low density polyethylene, ultra-low density polyethylene, linear low-density polyethylene, and high-density polyethylene are suitable polyethylenes for backsheets. Other suitable for use herein include, but not limited to, INSITE, available from Dow Chemical Company, of Midland, Mich., or EXXACT, available from the Exxon Chemical Company, of Bay City, Tex.

Other suitable thermoplastic polymers include polyesters, polyurethanes, polyamides, compostable or biodegradable polymers, heat-shrinkable polymers, thermoplastic elastomers, and metallocene-catalyst-based polymers, copolymers of the above-mentioned polymers, and mixtures thereof. Nonlimiting examples include polyurethanes such as ESTANE, available from B.F.Goodrich & Company of Cleveland, Ohio, and PELLETHANE, available from Dow Chemical Company of Midland, Mich.; polyamides such as PEBAX, available from Elf Atochem of Philadelphia, Pa.; polyesters such as HYTREL, available from DuPont de Nemours & Company of Wilmington, Del., ARNITEL, available from DSM Engineering Plastics of Evansville, Ind., and ECDEL, available from Eastman Company of Kingsport, Tenn. Exemplary compostable or biodegradable polymers are disclosed in U.S. Pat. application Ser. No. 09/520,676, filed on Mar. 7, 2000, and in U.S. provisional patent application (Attorney docket no. 8209P) filed on Aug. 17, 2000, both in the name of Zhao et al., the disclosure of which is hereby incorporated by reference.

Some of these polymeric films are breathable via activated diffusion of the moisture vapor through favorable molecular interactions and molecular architecture of the polymeric material. The breathability of such polymeric films can be further improved by creating micropores in the film using the process disclosed herein, whereby the moisture vapor can be more readily transmit through the apertures, voids, or pores.

A particularly suitable film 11 is a linear, low density polyethylene film that can have a thickness of from about 0.25 mils to about 5 mils, preferably a thickness of from about 0.25 mils to about 2.5 mils, and most preferably a thickness of from about 0.5 mils to about 1.5 mils.

In carrying out a method of making a composite, breathable, cloth-like backsheet in accordance with the present invention, breathability can be imparted to precursor film 11 before attachment of the film to nonwoven web 9, subsequent to its attachment to the nonwoven web, or both prior to and, if desired, subsequent to its attachment to the nonwoven web. The precursor film and/or the precursor film/nonwoven composite can be activated at modification station 16 to provide breathability to the precursor film by passing the film or the composite between a pair of opposed, interengaged forming rolls 14, 17 having any of the roll structures and roll surface configurations generally described earlier herein and shown in FIGS. 2, 6, 10, 11, and 12. The passing between such forming rolls of the precursor film, or of the precursor film and nonwoven laminate, can be repeated any number of times, and in any combination of the forming roll patterns hereinbefore described, until the desired composite web properties are attained.

Figure 13:
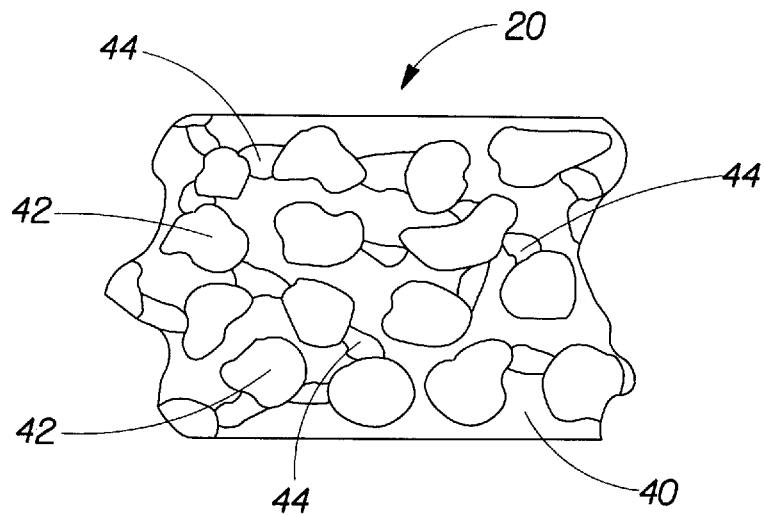
FIG. 13 is an enlarged, fragmentary, diagrammatic, cross-sectional view of a portion of a microporous film after the film has passed through a pair of forming rolls, to impart breathability to the film.

When a precursor film is passed between forming rolls having roll surface configurations of any of the types described herein, the interactions between the roll surface and the film provide localized stretching of the precursor film which results in the formation of micropores in the film. FIG. 13 shows a film after micropores have been formed, the polymeric component 40 of the film is extensible to a certain degree without rupture, whereas the pore forming agent 42 of the film is not extensible to any significant degree. Initially, polymeric component 40 provides a polymeric matrix that substantially completely surrounds and contacts the outer surfaces of pore forming agents 42. When the precursor film is stretched by a local incremental tensile force, such as by passage of the film between interengaged forming rolls of the types hereinbefore described, the extensible polymeric component 40 of the film becomes stretched locally. As a result, the polymeric component pulls away from and ultimately at least partially separates from some of the surfaces of the substantially inextensible pore forming agents 42 to cause the formation of a plurality of local voids or open areas 44 that are devoid both of the polymer and of the pore forming agent. The separation occurs at portions of the interfaces between polymeric component 40 and the peripheral surfaces of pore forming agents 42, most likely at the weak interfacial bonding sites between them. Typically, the micropores are irregularly configured and are irregularly distributed throughout the stretched areas of the film.

The micropores that are so developed by stretching the precursor film are of such a size that they are sufficiently large to permit passage through the film of air and moisture vapor, imparting the attribute of breathability to the film. However, preferably they are not so large as to allow the passage of liquids through the film. Thus, the micropores preferably have a mean pore size of less than about 0.4 microns, and more preferably less than 0.3 microns. In a preferred embodiment, the mean pore size may range from about 0.1 microns to about 0.25 microns.

The distribution of open areas 44 is also preferably such that at least some of the open areas are in communication with other, adjacent open areas to define flow paths that extend through the modified film from one surface to the other. In that respect, the interconnected micropores creates a capillaries system within the modified film to allow breathability, that is, permitting the passage of air and moisture vapor. The larger the pores/capillaries, the higher the breathability. However, for a web suitable for use as a breathable component (e.g., a backsheet) of an absorbent article, it must also be substantially imperviousness to the passage of liquids therethrough. If the capillaries are too large, there would be no meaningful discrimination between liquid permeability and water vapor/air permeability. Thus, there needs to be a balance between increasing breathability and maintaining liquid impermeability.

Furthermore, if the capillaries are small and hydrophobic. A certain amount of pressure is needed to fill the small capillaries with water. The smaller the capillary, the greater the pressure required to force the liquid into the capillary. The pressure of particular concern is that encountered by an absorbent article during wear, which may be imposed by wearer's motions such as sitting, lying, bending. Thus, for a modified web to simultaneously provide breathability and satisfactory leakage performance, the large capillaries in the web should be small enough such that they do not get filled with fluid under the pressure encountered during wear. In that respect, a few large capillaries are likely to have significantly adverse effect on the impact leakage performance of the modified web. Thus, the average pore/capillary sizes are not as indicative of leakage performance as the population of the large size pores/capillaries. The preferred microporous web should have few large capillaries, preferably the capillary diameters are less than 0.3 microns, more preferably less than 0.2 microns, and most preferably less than 0.1 microns. It is known that both the capillary diameter and the surface tension between the fluid and the capillary walls affect the leakage performance. Therefore, the web should preferably be made of hydrophobic material which provides a sufficiently high surface tension within the capillary to resist being filled by liquids at low pressures. Webs made of polyolefin polymers or blends are generally hydrophobic and are particularly preferred.

The incremental stretching process using the roll configurations disclosed herein is particularly useful for modifying the web to achieve the balanced properties of breathability and liquid impermeability, because fewer large pores and capillaries are formed by the incremental stretching process. It is found that further improvements in properties can be achieved by controlling certain process parameters. For example, applicants have found that by heating the web to a sufficient temperature above ambient while undergoing the incremental stretching operation and controlling other process parameters such as local strain rate, tooling parameters, and web speed, particularly beneficial results can be obtained. Most significantly, the properly controlled process parameters suppress or reduce the formation of large pores/capillaries that are detrimental to fluid imperviousness.

As discussed above, in an incremental stretching process of the present invention, there is a nonuniform distribution of local strains over the span between adjacent teeth, resulting in an unstretched web portion 30, a drawn portion 32 and an intermediate or neck portion 31.

Applicants have found that the pore initiation and growth in the neck region follows a "rapid nucleation" mode. That is, multiple micropores are initiated simultaneously by the pore forming agents dispersed in the polymeric matrix material. As such, the total applied stress is distributed substantially uniformly among the growing micropores. The resulting microporous web tends to have a multiplicity of relatively small pores of fairly uniform sizes, and the network of capillaries formed thereof is also of uniform diameters. As discussed above, such a microporous web has good breathability and good fluid impermeability.

In contrast, in a non-incremental stretching process where stresses are applied at far-apart or peripheral portions of a web, the web material is uniformly stretched without much necking. The pore initiation and growth in the uniformly stretched material follows a "slow nucleation" mode. A few micropores are initiated by the pore forming agents. These pore initiation sites become the weak or stress concentration points, leading to accelerated pore growth at these sites. Thus, the web material undergoes different pore growth rates at different sites. The resultant microporous web has inhomogeneous pore sizes and channel diameters; the early pore initiation sites have become disproportionately large. Such a web is highly breathable, but it also tends to have serious leakage problem. Exemplary non-incremental stretching process include tentering or rolling with toothless rolls.

One process parameter that can be used beneficially in the modification process disclosed herein is the temperature of the web being modified. It is found that when the web is modified at a temperature sufficiently above ambient, the intermediate web portion 31, where the deformation of the web material and pore initiation/growth occur, expands. Thus, more of the favorably-sized pores and channels are formed in the wider neck zone in the intermediate web portion, resulting in higher breathability while maintaining the liquid impermeability. The web temperature should typically be at least about 45° C., preferably at least about 55° C. and more preferably at least 65° C. The elevated web temperature can be achieved by preheating the web, heating the tooling, or both. Depending on the polymeric material used in the web, the temperature of the web should not be so high such that the web softens or melts to the extent that the web loses its mechanical strength substantially. Typically, the web temperature should be no more than about 120° C., preferably no more than about 105° C., and more preferably no more than about 90° C. For webs of polyolefin materials, a web temperature ranging from about 45° C. to about 95° C. is preferred.

Another useful process parameter is the engineering strain rate as calculated below. In a modification process according to the present invention, a precursor web passes between at least one pair of interengaging rolls where the teeth on the roll surface stretch the web incrementally.

Figure 16:
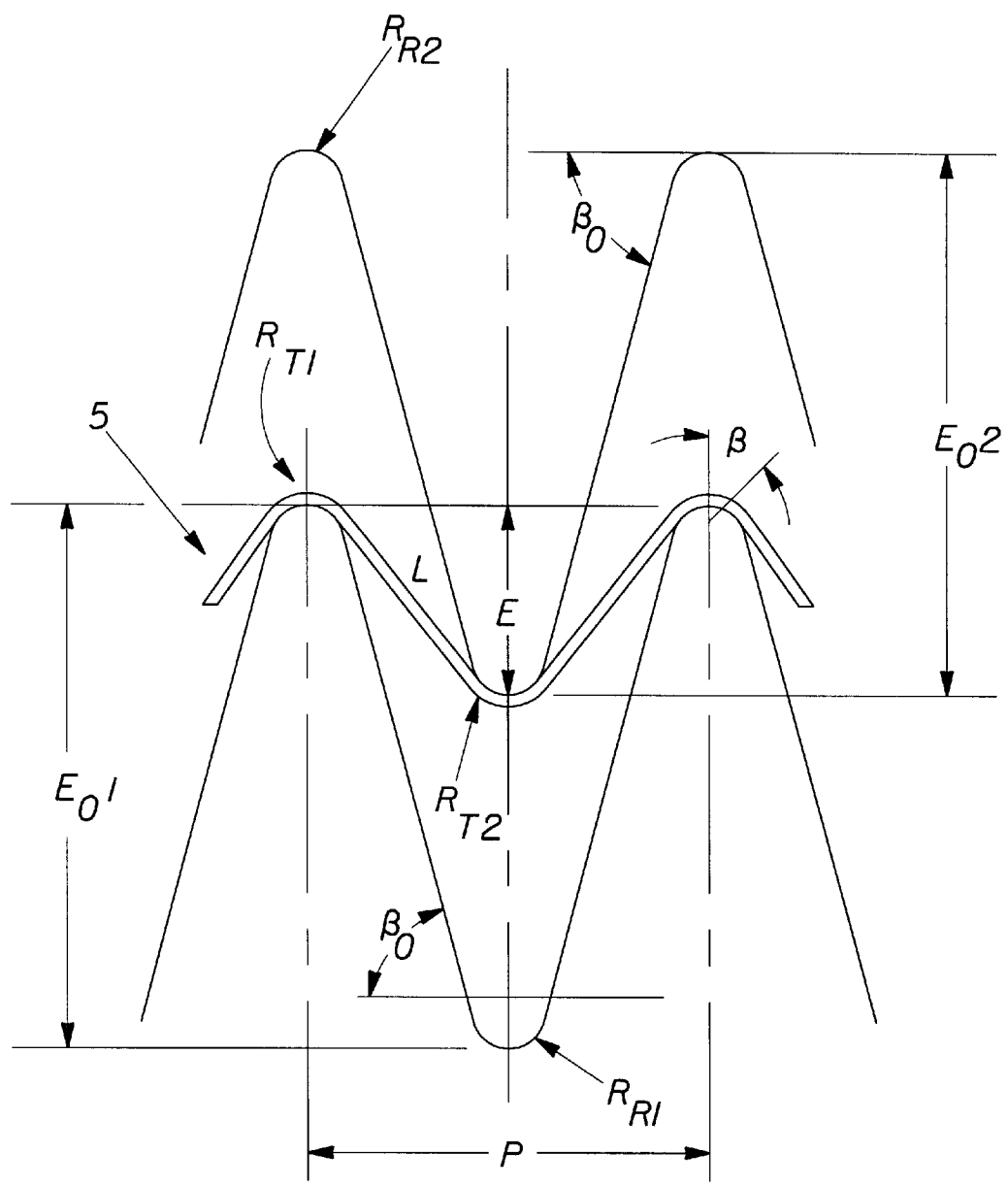
FIG. 16 is a schematic illustration of the tooling and operating parameters that contribute to the engineering strain rate.

FIG. 16 shows a representative geometry for teeth on two interengaging rolls, wherein $R_{T1}$ and $R_{T2}$ are the tip radii of the teeth profiles, P is the tooth pitch, and E is the depth of engagement.

The engagement depth E is a function of time:

$$E(t) = E - Di \cdot \left[1 - \cos\left[\left[\frac{t}{(2 \cdot T)}\right] \cdot \left(2 \cdot a\cos\left(1 - \frac{E}{Di}\right)\right) - a\cos\left(1 - \frac{E}{Di}\right)\right]\right]$$

wherein Di is the roll diameter, and t has a value ranging from zero (at the initiation of engagement) to T (at total engagement or just prior to the initiation of disengagement). T can be calculated as below:

$$T = a\cos\left(1 - \frac{E}{Di}\right) \cdot \frac{Di}{2 \cdot Vw}$$

The average local strain, Strain(t), is dependent on the pitch P, the length between the tangent of the tooth tips L(t) and the wrap length on tooth tips S(t):

$$L(t)=[(E(t)-RT1-RT2)^2-(0.5 \cdot P)^2-(RT1+RT2)^2]^{0.5}$$

$$S(t) = (RT1 + RT2)\left[3.14159 - a\tan\left[0.5\frac{P}{(E(t) - RT1 - RT2)}\right] - a\cos\left[\frac{(RT1 + RT2)}{[(E(t) - RT1 - RT2)^2 + (0.5P)^2]^{0.5}}\right]\right]$$

$$\text{Strain } (t) = \left[\frac{2 \cdot (L(t) + S(t))}{P} - 1\right] \cdot 100$$

The average local strain rate can be calculated by taking the derivative of the average local strain, and the engineering strain rate is calculated by setting the second derivative of the average local strain to zero (i.e., the maximum of the average local strain rate versus time curve). As shown above, the engineering strain rate is a function of several tooling and operating variables, including roll diameter, tooling pitch (which determines the span between neighboring teeth), depth of engagement of the teeth, roll diameter, web speed (which determines the engagement speed), and tooth tip radius. Exemplary rolls suitable for use herein may have diameters of about 6 to about 24 inches (15.24 to 60.96 cm), tooth pitch of about 0.030 to about 0.100 inch (0.762 to 2.54 mm), and tooth tip radius of about 0.004 to about 0.006 inch (0.102 to 0.152 mm).

Modified web having satisfactory properties (such as water vapor/air breathability and liquid impermeability) can be obtained via a local stretching process at room temperature when the engineering strain rate is optimized. For example, a polyolefin web can be modified to have desirable moisture vapor transmission rate(MVTR) and liquid impact value. Typically a MVTR of at least 2000 g/m$^2$/24 hr and a liquid impact value of less than 10 g/m$^2$ can be achieved when the web is modified at a temperature from ambient to 110° C., and preferably from about 45° C. to about 95° C., and an engineering strain rate in the range from about 50 s$^{-1}$ to about 1650 s$^{-1}$, preferably from about 150 s$^{-1}$ to about 1100 s$^{-1}$, and more preferably from about 350 s$^{-1}$ to about 900 s$^{-1}$. Modified web having desirable properties can be achieved at a minimum web speed of about 30 m/min, and a maximum web speed up to about 150 m/min, preferably up to 300m/min and more preferably up to 365 m/min. Thus, the present invention provides an economic method of manufacturing a breathable, liquid impermeable and cloth-like web at high line speed.

JOINING NONWOVEN WEB WITH FILM TO FORM A LAMINATE

Figure 9:
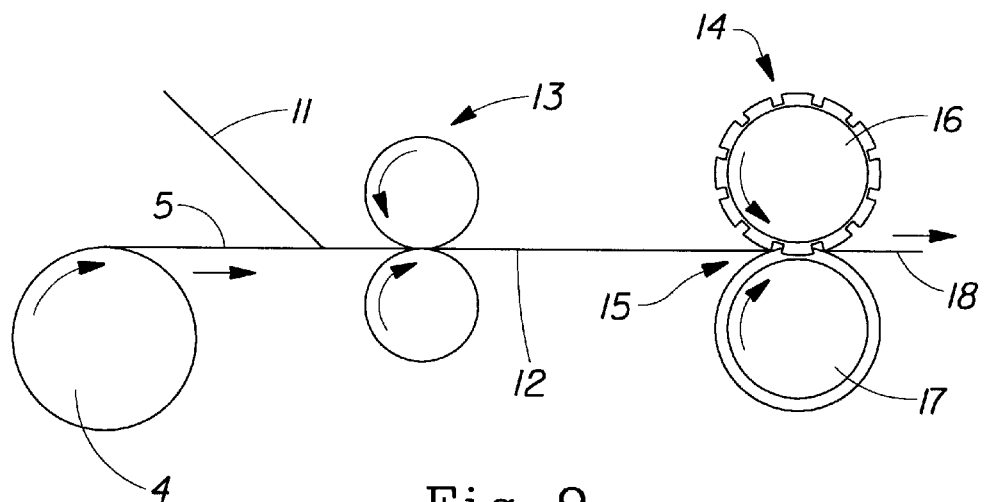
FIG. 9 is a schematic illustration of an exemplary process and apparatus for joining and modifying a composite web material in accordance with the present invention.

FIG. 9 shows another aspect of the present invention the joining to one surface of a nonwoven web 5 at joining station 13 of a polymeric film 11 to provide a composite web 12 that can be utilized as a backsheet for a disposable absorbent article, such as a disposable diaper, or the like. Film 11 can be a polyolefin film, preferably a polyethylene film, and forms one layer of a composite backsheet that includes a liquid-impervious barrier film and at least one layer of a thin, nonwoven sheet that is attached to at least one surface of the film.

One or both web 5 and polymeric film 11 of FIG. 9 may be a precursor web or film which can be modified to have increased breathability by suitable treatment of the web or film as described in the present invention. Alternatively, one or both web 5 and polymeric film 11 may be modified prior to being joined into a laminate.

The film material can be joined to the nonwoven material at joining station 13 in a number of ways, including thermal lamination, adhesive lamination, direct lamination by extrusion, and vacuum lamination, each of which methods is well known to those skilled in the art. The film material can be a pre-formed film and can be modified, as previously described, to impart breathability at a time before it is joined with the nonwoven material. Preferably, film 11 and nonwoven 5 are joined before the film is made breathable, after which the resulting composite web 12 can be passed between suitable forming rolls at modification station 16 to locally stretch the composite web, thereby provide breathability to the film component of the composite web. This allows the properties of the nonwoven web to be modified as desired without simultaneously undesirably effecting the structural integrity of the film and/or the composite.

The joining of a non-fibrous polymeric film with a fibrous nonwoven web to form a composite web can be effected by heating either or both of the web or film to its softening temperature, and then pressing the web and film together lightly so that the web and film adhere to each other sufficiently to form a coherent, unitary, composite web upon cooling. Pressing can be performed at joining station 13 shown in FIG. 9. Alternatively, instead of heating one or both the web or the film, the components of the composite web can be joined by applying to either of the materials a suitable adhesive, such as adhesive H2511, available from Findley Adhesives, Inc., of Milwaukee, Wis., and by then lightly pressing the materials together at joining station 13 so that they adhere to each other sufficiently to form a coherent composite web after the adhesive sets. When adhesive is utilized to join the materials together, the adhesive is preferably applied to one or both of the materials in a discontinuous pattern, in order not to completely coat an unactivated precursor film, and in order not to fill all the micropores at the surface of a previously-activated precursor film.

As a further variant of the method of joining a polymeric precursor material with a nonwoven web, a layer of polymeric precursor material can be extrusion coated onto one of the surfaces of the nonwoven web. In that instance, because of the elevated temperature of the polymeric material as it exits from an extruder onto the nonwoven web, the extruded material is sufficiently tacky so that it adheres to at least portions of the surface of the nonwoven web. If the temperature of the extruded material is sufficiently high, some melting of surface fibers of the nonwoven web can also take place, which upon cooling provides an even stronger bond between the polymeric precursor material and the nonwoven web.

In an another method, a polymeric precursor film can be applied to a surface of the nonwoven web by vacuum lamination of the precursor film material onto the modified web.

The resulting composite web structure can then be passed between a pair of opposed, interengaging forming rolls 16, 17 at modification station 14. The forming rolls of station 16 can have a surface configuration and a structural arrangement similar to those forming rolls disclosed hereinabove. It is found that the interactions between the film and the nonwoven web during stretching promote "rapid nucleation" mode of pore formation in the film component. Without being bound by theory, it is believed that these interactions between the film and the nonwoven web are analogous to, but on a much finer scale, the contacts between the teeth and the web surface that provide nonuniform local strains and a multitude of neck regions, resulting in more uniform pore and capillary sizes. Additionally, the finer scale contacts in a laminate also render the laminate more responsive to factors that promote necking (e.g., temperature).

An additional rolling step can be employed, if desired, to expand the modified composite web 18 laterally, to further reduce its basis weight and thereby its cost per unit area. The shapes of the teeth and grooves, the spacing of the axes of the forming rolls, and the degree of interengagement of the opposed teeth and grooves of the second set of forming rolls are such that the cross-web width of the exiting composite web is preferably from about 10% to about 200% of that of the entering composite web, more preferably from about 10% to about 100%, and most preferably from about 10% to about 50%.

MODIFIED WEBS AS DISPOSABLE DIAPER COMPONENTS

A modified web of the present invention typically provides a MVTR of at least 2000 g/m$^2$/24 hr, preferably at least 3000 g/m$^2$/24 hr, and more preferably at least 4000 g/m$^2$/24 hr, and a dynamic fluid impact value of less than 10 g/m$^2$, preferably less than 7 g/m$^2$, more preferably less than 5 g/m$^2$, and most preferably less than 3 g/m$^2$.

Another measure of fluid impermeability of the modified web is the bubble pressure. When the capillaries of the specimen are completely filled with a low surface tension fluid, there is essentially no air flow until sufficient air pressure is applied to force the fluid out of the largest capillaries in the specimen. The breakthrough pressure is called "bubble pressure" of the specimen, and is dependent on the size of the capillaries in the specimen. The larger size capillaries are the ones more likely to permit fluids flow through during diaper wear. A modified web of the present invention typically has a bubble pressure of at least about 45 psi, preferably of at least 60 psi, and more preferably of at least 70 psi.

Another measure of the breathability of the modified web is its ability to allow air flow at moderate pressure differential across the web. Whereas MVTR is a measure of the convective flow of water moisture or air through the web, air flow is a measure of the forced flow of water moisture or air through the web. Thus, air flow measurement simulates the conditions where a pressure is imposed on the absorbent article by wearer motions such as sitting, lying, bending, and the like. A modified film of the present invention typically has an air flow value, measured at 20 psi differential pressure, of at least 2 liters/m$^2$/s, preferably of at least 3.5 liters/m$^2$/s, and more preferably of at least 5 liters/m$^2$/s.

In forming a cloth-like, texturized web, the web is deformed or stretched beyond the elastic limit of the web, resulting in a plurality of raised, rib-like elements. A measure of the increase in the web's surface contour length after the modification is the percent set. To provide the desirable comfort and fit of an article using the modified web of the present invention, the modified web typically has a percent set value of at least about 20%, preferably at least about 40%, and more preferably at least about 60%. In a preferred embodiment, the modified web has a percent set value from about 40% to about 120%.

As noted previously herein, composite structures including a modified webs and made in accordance with the present invention can be advantageously utilized as a component of a disposable diaper. The component is generally the outermost component of the article, such as a backsheet, and provides imperviousness to the passage of liquid body exudates that are intended to be absorbed by and retained in an absorptive component of the article. In the embodiment of a backsheet, the modified web provides desirable imperviousness to the passage of fluids, while permitting passage therethrough moisture vapor and air. Additionally, as a backsheet, the modified web is preferably flexible, compliant, and has the desired soft, cloth-like outer surface texture. The ensuing discussion provides additional information relating to the structure of such articles.

As used herein in the context of disposable absorbent articles, the term "absorbent article" refers generally to devices that absorb and contain body exudates. More specifically, it refers to devices that are placed against or in proximity to the body of a wearer to absorb and contain the various exudates discharged from the body. Exemplary absorbent articles include diapers, training pants, feminine pads, pantiliners, and adult incontinence articles.

As used herein, the term "disposable" means absorbent articles that are not intended to be laundered or otherwise restored or reused as an absorbent article (i.e., they are intended to be discarded after a single use and, preferably, to be recycled, composted, or otherwise disposed of in an environmentally compatible manner).

Figure 15:
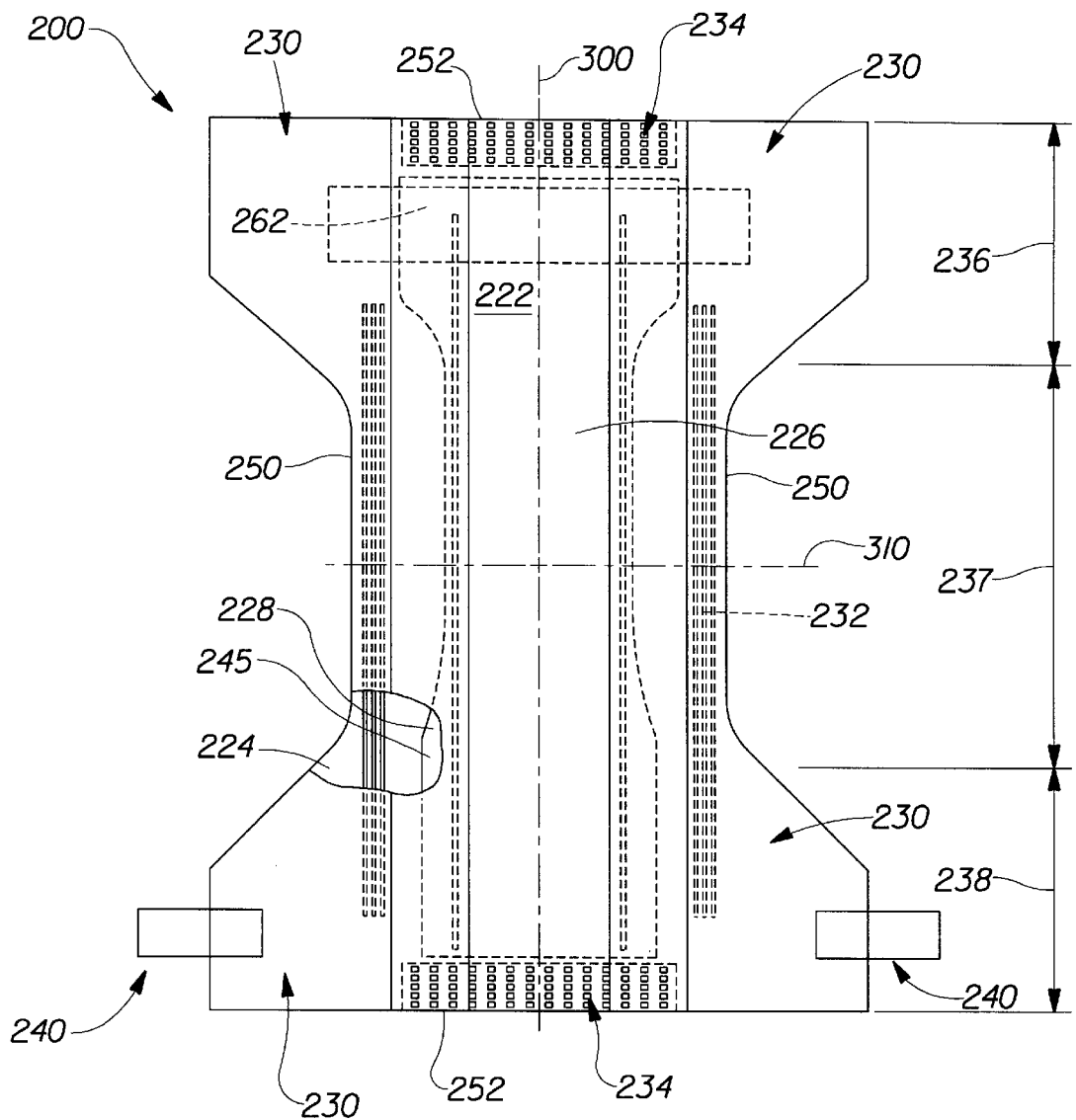
FIG. 15 is a plan view of a disposable diaper that includes structural components which incorporate a modified web in accordance with the present invention.

An embodiment of a disposable absorbent article is shown in FIG. 15 in the form of disposable diaper 200. As used herein, the term "diaper" refers to an absorbent article generally worn about the lower torso by infants and incontinent persons. However, the present invention is also applicable to other forms of absorbent articles, such as incontinence briefs, incontinence undergarments, absorbent inserts, diaper holders and liners, pull-on diapers and training pants, feminine hygiene garments, and the like.

FIG. 15 is a plan view of diaper 200 while in a flat-out state, and with a portion of the structure broken away to more clearly show the overall construction of the article. As it is represented in FIG. 15, the portion of diaper 200 that faces the body of the wearer faces away from the viewer of that Figure, and the portion of the diaper that faces outwardly from the wearer, toward the wearer's outer garments, faces the viewer of FIG. 15. As shown, diaper 200 includes a liquid-pervious topsheet 224; a liquid impervious backsheet 226; an absorbent core 228, which is preferably positioned between at least a portion of topsheet 224 and backsheet 226; side panels 230; elasticized leg cuffs 232; an elastic waist feature 234; and a fastening system generally designated 240.

Diaper 200 includes a chassis 222 that defines the main body of the diaper. Chassis 222 includes at least a portion of absorbent core 228, and also preferably includes outer covering layers formed by topsheet 224 and backsheet 226. If the absorbent article includes a separate holder and a separate liner, chassis 222 generally also includes the holder and the liner. For example, a holder can include one or more layers of material to form an outer cover of the article, and a liner can include an absorbent assembly including a topsheet, a backsheet, and an absorbent core. In such cases, the holder and/or the liner can include a fastening element that is used to hold the liner in place throughout the time of use. For unitary absorbent articles, however, chassis 222 is the main structural component of the diaper, with other features added to form the overall diaper structure shown.

Backsheet 226 is generally that portion of diaper 200 that is positioned adjacent the garment facing surface 245 of absorbent core 228 and that serves to prevent body exudates that are absorbed and contained in absorbent core 228 from soiling articles that may come into contact with diaper 200, such as bedsheets and undergarments.

Although topsheet 224, backsheet 226, and absorbent core 228 can be assembled in a variety of well-known configurations, preferred diaper configurations are described generally in U.S. Pat. No. 3,860,003, entitled "Contractible Side Portions for Disposable Diaper," which issued to Kenneth B. Buell on Jan. 14, 1975; U.S. Pat. No. 5,151,092, entitled "Absorbent Article with Dynamic Elastic Waist Feature Having a Predisposed Resilient Flexural Hinge," which issued to Buell et al. on Sep. 29, 1992; U.S. Pat. No. 5,221,274, entitled "Absorbent Article with Dynamic Elastic Waist Feature Having a Predisposed Resilient Flexural Hinge," which issued to Buell et al. on Jun. 22, 1993; U.S. Pat. No. 5,554,145, entitled "Absorbent Article With Multiple Zone Structural Elastic-Like Film Web Extensible Waist Feature," which issued to Roe et al. on Sep. 10, 1996; U.S. Pat. No. 5,569,234, entitled "Disposable Pull-On Pant," which issued to Buell et al. on Oct. 29, 1996; U.S. Pat. No. 5,580,411, entitled "Zero Scrap Method For Manufacturing Side Panels For Absorbent Articles," which issued to Nease et al. on Dec. 3, 1996; and U.S. patent application Ser. No. 5,899,895, entitled "Absorbent Article With Multi-Directional Extensible Side Panels," issued May 4, 1999, to Robles et al. The disclosures of each of the foregoing patents and patent application are incorporated herein by reference.

The modified web of the present invention can be employed as a backsheet 226, as shown in FIG. 15. In one embodiment, the backsheet 226 may be a film that is pervious to moisture vapor, preferably pervious to air, and also substantially impervious to liquids, as hereinabove described. For example, a breathable film or a precursor film that is thereafter rendered breathable can be joined with a modified nonwoven, as described earlier herein. A breathable backsheet can provide a barrier to the passage of liquids through the backsheet while allowing the passage of moisture vapor, and preferably air, which increases the comfort to the wearer by enabling the reduction of the relative humidity level inside the diaper as it is worn. in another embodiment, the backsheet can be a composite backsheet formed from a film joined with a nonwoven web. The nonwoven can be the outwardly-facing surface of the diaper for softness and cloth-like external appearance, and the impervious film can provide a barrier to prevent absorbed waste matter from contacting the clothing worn by a user, or from contacting bedding if worn by a user while sleeping.

TEST METHODS

Components such as backsheets for disposable absorbent articles preferably have moisture vapor transmission rates, dynamic fluid impact values, and desirably oxygen permeation rates that fall within preferred ranges. The test methods for determining the values of those parameters for particular materials are described below.

Moisture Vapor Transmission Rate Determination

One measure of the breathability of a film or composite material is the perviousness of the film or composite to the passage of water vapor, reflected by the moisture vapor transmission rate (MVTR) of the film. In the case of disposable diapers, breathability can be imparted to, for example, a composite backsheet by the process hereinabove described, or by employing a film in the composite which already possesses such a quality, as also described hereinabove. In that regard, the MVTR of the composite material, such as a backsheet, is preferably from about 500 g/m²/24 hr to about 5000 g/m²/24 hr, more preferably from about 1000 g/m²/24 hr to 4000 g/m2/24 hr, and most preferably from about 2000 g/m²/24 hr to about 3000 g/m2/24 hr.

The MVTR can be determined by placing a quantity of a hydrophilic material, such as calcium chloride, into a non-porous, open-top vessel (not shown) having an outwardly-extending flange around the vessel opening. A portion of the material for which the MVTR is to be determined is placed in overlying relationship relative to the vessel opening and is in contact with the flange of the vessel to completely cover the open end of the vessel. An annular gasket and an annular retaining ring are then placed over the material to be tested and are securely clamped to the vessel flange by any convenient clamping arrangement, to tightly and completely seal the periphery of the vessel opening in order that transmission of air or moisture vapor can only occur through the material under test. The resulting assembly is then weighed to determine the initial weight of the vessel and its contents.

After the initial weight has been determined, the assembly is placed in a chamber having a constant temperature (40° C.) and a constant humidity (75% relative humidity). The vessel is maintained under those atmospheric conditions for a period of five (5) hours, after which it is removed from the chamber, wrapped tightly with an impervious film to prevent transfer of moisture into and out of the vessel, and is allowed to reach thermal equilibrium with the ambient atmosphere in which the weigh balance is located. Thermal equilibrium is achieved in about 30 minutes, after which the film overwrap is removed from the vessel, which is again weighed to determine the final weight of the vessel and its contents.

The MVTR is calculated by the following formula, which provides the MVTR in g/m²/24 hr:

$$MVTR = \frac{(\text{Final Wt (gm)} - \text{Initial Wt (gm)}) \times 24.0}{\text{Sample Area (sq. meters)} \times 5.0 \text{ hr.}}$$

Dynamic Fluid Impact Value Determination

When imparting a limited degree of moisture vapor, and also preferably air perviousness to a component such as a backsheet, it is important that the imperviousness of the component to liquids is not significantly diminished. And in addition to the desired attributes of imperviousness to liquids and perviousness to moisture vapor and preferably air when a component such as a backsheet is under no-load conditions, it is also desirable that substantial liquid imperviousness of the component be maintained even when the absorbent article is subjected to impact loads. Such loads can be imposed, for example, on a diaper backsheet when a baby wearing the diaper abruptly goes from a standing to a sitting position. In that regard, it is preferred that the perviousness to liquids under impact conditions be less than about 10 g/m², more preferably less than about 5 g/m², and most preferably less than about 2.5 g/m².

Perviousness of a material under impact conditions can be assessed by a test the measures the dynamic impact value of the material. As referred to herein, the "dynamic impact value" of a material is a value that is based upon the impact energy an average 20 lb. baby will impart to a saturated diaper if he or she falls or abruptly shifts from a standing position to a sitting position. Essentially, the dynamic impact value is a measure of the quantity of liquid that penetrates through a material under impact conditions.

Figure 14:
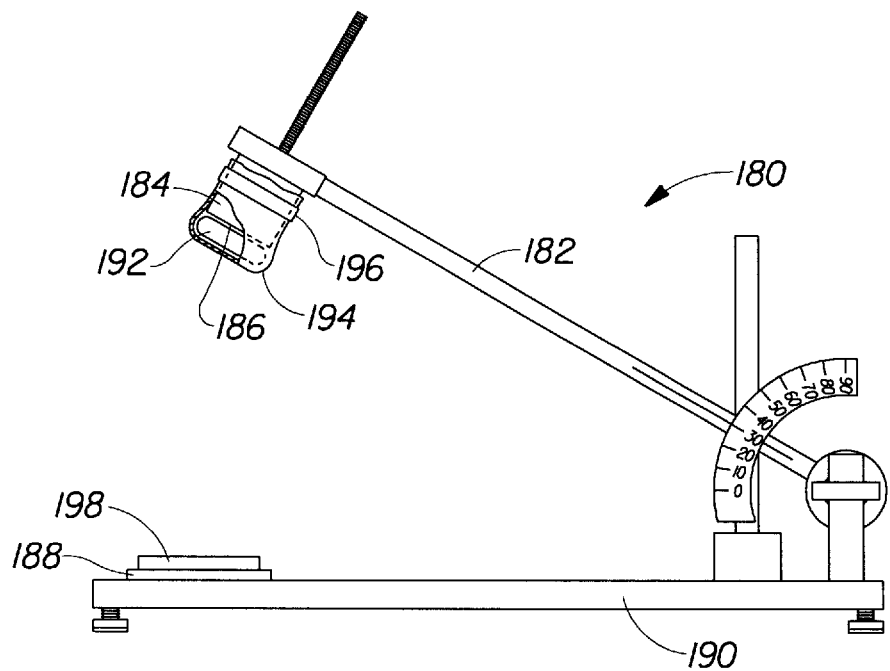
FIG. 14 is an elevational view of apparatus used in a method for determining the dynamic impact value of a material as an assessment of its perviousness to liquids when subjected to impact conditions.

Determination of the dynamic impact value for a particular material can be made by applying to the material an impact load of 20 Joules (14.75 ft-lb.) over an area of about 13.5 in², or 2300 Joules/m². Impact loading of a test specimen can be performed in a number of ways, such as by a device 180 shown in FIG. 14. Device 180 includes a pivotable lever 182 that has a weight 184 at its outer end.

Weight 184 has an impact area of 0.00317 m² to contact a test specimen 186. To simulate the skin and body fat of a baby a foam impact pad 188 is positioned on base 190 of device 180 and opposite weight 184. A suitable foam pad is available from American Excelsior Corp., of Cincinnati, Ohio, and is a 1 in. thick polyurethane foam pad undergoes 15.3% compression at a 1 psi. applied load. Impact pad 188 is preferably a crosslinked rubber foam pad, about 5 in. by 5 in., is carbon black filled, has a density of 0.1132 g/cm³, and has a thickness of 0.3125 in.

A wet diaper is simulated by providing a circular pad 192 in the form of a 2.5 in diameter section of CMC517 material available from Weyerhaeuser Inc. of Columbus, Miss. Pad 192 has a basis weight of 228 g/m², and a caliper of 0.127 in. measured under a 0.2 psi. load. The pad is saturated with simulated urine (Triton X-100, 0.0025% (wt/vol), and available from Union Carbide Corp., of Danbury, Conn.) so that the saturated pad has a weight 10 times that of the dry pad.

Circular pad 192 is saturated and is held against the impact surface of weight 184 by the material 184 for which the impact perviousness is to be determined. In that regard, a 10 in. by 10 in. test sheet of material can be provided, with the outside surface of the material (i.e., that surface of the material which would be an outside surface of an absorbent article) facing downwardly. Material 194 is applied over pad 192 and is attached to the impact surface of weight 184 by a rubber band 196, or the like.

Weight 184 is adapted to impact a piece of dry filter paper 198, which can, for example, be a filter paper obtained from Whatman Inc, of Haverhill, Mass., (#2 filter paper, approximately 100 mm. diameter, Whatman Catalog No. 1002 150). The initial weight of the dry filter paper is determined, and the filter is placed in position on energy absorbing impact pad 188 that is positioned on base 190.

Weight 184 with its simulated diaper (saturated core 192 and overlying backsheet material 186) is dropped onto the filter paper from a height calculated to provide the desired impact load to the simulated diaper. Any liquid that passes through the material as a result of the impact is received on the filter paper. Weight 184 is permitted to remain in place on filter paper 198 for a period of 2 minutes after impact. Thereafter, the impacted filter paper is placed on a scale, and when three minutes from the time of impact have elapsed the weight of the impacted filter paper is determined. The dynamic impact value is calculated from the following formula:

$$DIV = \frac{\text{Filter Mass Change (grams)}}{\text{Impact Area (sq. meters)}}$$

Air Flow Rate

The air flow rate of the material can be determined by placing a portion of the material between a sintered stainless steel disk (having high porosity and a pore size in the 5–10μm range) and an annular gasket, and clamped securely into the testing fixture of a capillary flow porometer (available from PMI, Ithaca, N.Y.). The flow porometer is programmed to measure the air flow rate across the specimen over a range of applied air pressures. The air flow rate of the film is determined by reading the air flow rate at 20 psi. For this measurement to be accurate, the air flow rate of the sintered stainless steel disk should be more than 100 times greater than that measured for the specimen. The specimen's air flow rate is expressed as the air flow rate in liters/second divided by the sample area inside the annular gasket in square meters.

Bubble Pressure

The bubble pressure of the material can be determined by completely filling the specimen's capillaries with a low surface tension PorewickTM(available from PMI, Ithaca N.Y.), placing the saturated specimen between a sintered stainless steel disk and an annular gasket, and clamped securely into the testing fixture of a capillary flow porometer (available from PMI, Ithaca, N.Y.). The capillary flow porometer is programmed to record the bubble pressure at a flow rate of 50 cc/minute and a V/PT factor of 30. For this measurement to be accurate, the pores of the sintered stainless steel disk should be greater than about three microns, and less than about 15 microns. The instrument records the specimen's bubble pressure automatically.

Percent Set Measurement Method

Percent Set provides a measure of the increase in the web's surface contour length after modification. This measurement is done by activating the web using the apparatus such as shown in FIG. 2. Before modification, a pair of lines 100 mm apart are drawn on the portion of the specimen perpendicular to the direction of web stretching. A suitable tensile testing apparatus equipped with a force transducer sensitive to small forces should be used. The grips (pneumatically actuated, flat-face type) are set to a gage length of 100 mm. The specimen is mounted so that the lines coincide with the edges of the grips. The load-displacement data are collected at a cross-head speed of 0.1 cm/second. The displacement at which the load increases above about 5 grams/cm of sample width is recorded. The specimen's percent set is recorded as $$\% \text{ set} = \frac{\text{dispacement (mm)}}{100 \text{ mm}} \times 100 \%$$

For a pre-activated web, that is, the web has been stretched in a pre-forming process prior to being modified by the forming process of the present invention, the percent set of the modified web is a "residual set".

EXAMPLES

Example 1

A polyethylene composition having calcium carbonate particles dispersed therein is extruded using a conventional extruder. A film web is of about 49 gsm gauge. The film web is then incrementally stretched according to the method disclosed herein and shown schematically on FIG. 1. The process uses 6 inch (15.24 cm) diameter forming rolls. The web and the tooling may be at ambient temperature or may be heated to a higher temperature as indicated. TABLE I shows the processing parameters and the properties of the resultant breathable web. The forming rolls have the tooth and groove configuration of FIG. 2.

TABLE I

| EXAMPLE | | | | |
|---|---|---|---|---|
| | I-a | I-b | I-c | I-d |
| Pitch (mm) | 1.52 | 1.52 | 1.52 | 0.76 |
| Engagement (mm) | 1.02 | 1.02 | 1.57 | 0.76 |
| Total Applied Strain (%) | 75 | 75 | 140 | 140 |
| Web Speed (meters/min) | 42 | 219 | 219 | 219 |

TABLE I-continued

| EXAMPLE | | | | |
|---|---|---|---|---|
| Web Temperature (C) | 65 | 65 | 65 | 65 |
| Engineering strain rate* (sec-1) | 93 | 480 | 770 | 1100 |
| MVTR (g/m2/day) | 3300 | 2600 | 4100 | 4000 |
| Dynamic Fluid Impact (gsm) | 5.4 | 2.7 | 1.8 | 4.0 |
| Set (%) | 30 | 30 | 72 | 93 |
| | I-e | I-f | | I-g |
| Pitch (mm) | 1.52 | 0.76 | | 1.52 |
| Engagement (mm) | 1.57 | 0.76 | | 1.57 |
| Total Applied Strain (%) | 140 | 140 | | 140 |
| Web Speed (meters/min) | 42 | 42 | | 219 |
| Web Temperature (C) | 25 | 25 | | 25 |
| Engineering strain rate* (sec-1) | 150 | 215 | | 770 |
| MVTR (g/m2/day) | 3200 | 3100 | | 2900 |
| Dynamic Fluid Impact (gsm) | 1.8 | 3.0 | | 0.5 |
| Set (%) | 66 | 65 | | 66 |

Example 2

A precursor laminate of nonwoven and film is prepared via adhesive bonding. The nonwoven is a carded nonwoven web of bi-component fibers having the configuration of a polyethylene sheath and a polypropylene core is used. The nonwoven web has a gauge of 22 gsm. The precursor (i.e., unmodified) film is made from polyethylene/calcium carbonate and has a gauge of about 46 gsm gauge, and is extrusion bonded to the nonwoven web. The unmodified laminate is incrementally stretched according to the method disclosed herein. The process is shown schematically on FIG. 9. The process uses 6 inch (15.24 cm) diameter forming rolls. The web and the tooling may be heated to a sufficiently high temperature as indicated. TABLE II shows the processing parameters and the properties of the resultant breathable web. The forming rolls have the tooth and groove configuration of FIG. 2.

TABLE II

| EXAMPLE | II-a | II-b | II-c |
|---|---|---|---|
| Pitch (mm) | 1.52 | 1.52 | 0.76 |
| Engagement (mm) | 1.02 | 1.57 | 0.76 |
| Total Applied Strain (%) | 75 | 140 | 140 |
| Web Speed (meters/min) | 42 | 42 | 42 |
| Web Temperature (C) | 65 | 65 | 65 |
| Engineering strain rate* (sec-1) | 93 | 150 | 215 |
| MVTR (g/m2/day) | 2300 | 3500 | 4000 |
| Dynamic Fluid Impact (gsm) | 1.0 | 4.0 | 3.2 |
| Set (%) | 20 | 59 | 82 |

Example 3

The unmodified laminate of Example 2 is pre-activated by a two-stage forming process. The first stage is a CD stretching and the second stage is a MD stretching. The pre-activation process uses forming rolls having a 6 inch(15.24 cm) diameter and a tooth and groove configuration of FIG. 2, and is operated at a web speed of about 150 m/min and a web temperature of about 60° C. The pre-activated laminate is then subjected to the forming process according to the present invention. The web and the tooling may be at ambient temperature or may be heated to a higher temperature as indicated. TABLE III shows the processing parameters and the properties of the resultant breathable web. The forming rolls have the tooth and groove configuration of FIG. 2.

TABLE III

| EXAMPLE | III-a | III-b | III-c |
|---|---|---|---|
| Pitch (mm) | 0.76 | 0.76 | 0.76 |
| Engagement (mm) | 0.38 | 0.38 | 0.38 |
| Total Applied Strain (%) | 45 | 45 | 45 |
| Web Speed (meters/min) | 219 | 219 | 219 |
| Web Temperature (C) | 25 | 65 | 95 |
| Engineering strain rate* (sec-1) | 500 | 500 | 500 |
| MVTR (g/m2/day) | 2300 | 2800 | 3100 |
| Dynamic Fluid Impact (gsm) | 1.4 | 1.8 | 1.6 |
| Residual Set (%) | 10 | 13 | 15 |

Example 4

The film web of Example 1 is incrementally stretched according to the method disclosed herein and shown schematically on FIG. 1. The process uses 6 inch (15.24 cm) diameter forming rolls. The web and the tooling are heated to a temperature of 65° C. TABLE IV shows the processing parameters and the properties of the resultant breathable web. The forming rolls have the tooth and groove configuration that produces a modified web as shown in FIG. 10.

TABLE IV

| EXAMPLE | IV-a | IV-b |
|---|---|---|
| Pitch (mm) | 1.02 | 1.02 |
| Engagement (mm) | 0.76 | 1.02 |
| Total Applied Strain (%) | 87 | 133 |
| Web Speed (meters/min) | 195 | 195 |
| Web Temperature (C) | 65 | 65 |
| Engineering strain rate* (sec-1) | 600 | 810 |
| MVTR (g/m2/day) | 3800 | 4600 |
| Dynamic Fluid Impact (gsm) | 2.8 | 4.1 |

Example 5

An unmodified laminate is incrementally stretched according to the method disclosed herein. The laminate included a carded nonwoven web of polypropylene fibers and a film of from polyethylene/calcium carbonate. The nonwoven web has a gauge of 18 gsm and the film has a gauge of about 35 gsm gauge and is extrusion bonded to the nonwoven web. The process uses 6 inch (15.24 cm) forming rolls. The web and the tooling are heated to 65° C. TABLE V shows the processing parameters and the properties of the resultant breathable web. The forming rolls have the tooth and groove configuration that produces a modified web as shown on FIG. 10.

TABLE V

| EXAMPLE | V-a | V-b | V-c | V-d |
|---|---|---|---|---|
| Pitch (mm) | 1.02 | 1.02 | 0.76 | 1.02 |
| Engagement (mm) | 0.64 | 0.76 | 1.02 | 1.02 |
| Total Applied Strain (%) | 66 | 87 | 87 | 133 |
| Web Speed (meters/min) | 30 | 30 | 195 | 195 |
| Web Temperature (C) | 65 | 65 | 65 | 65 |
| Engineering strain rate* (sec-1) | 74 | 92 | 600 | 810 |
| MVTR (g/m2/day) | 2700 | 3900 | 2700 | 3500 |
| Dynamic Fluid Impact (gsm) | 2.4 | 4.3 | 2.4 | 6.1 |

Example VI

This example illustrates that suitable control of process parameters can lead to an especially desirable properties in the resultant film webs. TABLE VI below illustrates the effect of process conditions and the beneficial properties of the resultant material. The material subjected to the process is a polyolefin/calcium carbonate film of 49 g/m².

|  | Example VI-a | Example VI-b |
|---|---|---|
| Pitch (mm) | 0.76 | 0.76 |
| Engagement (mm) | 0.51 | 0.76 |
| Total Applied Strain (%) | 75 | 140 |
| Web Speed (meters/min) | 42 | 216 |
| Web Temperature (C) | 65 | 25 |
| Engineering strain rate* (sec-1) | 140 | 1100 |
| MVTR (g/m2/day) | 3300 | 2500 |
| Dynamic Fluid Impact (gsm) | 2.3 | 2 |
| Air Flow (l/m2/s) | 2.2 | 3.9 |
| Bubble Pressure (psi) | 74.8 | 77.7 |
| Set (%) | 40 | 63 |

Although particular embodiments of the present invention have been illustrated and described, it will be apparent to those skilled in the art that various changes and modifications can be made without departing from the spirit of the present invention. Accordingly, it is intended to encompass within the appended claims all such changes and modifications that fall within the scope of the present invention.

What is claimed is:

1. A method of making a breathable web comprising:
   a. feeding a web of a polymeric film having a pore forming agent dispersed therein in a web movement direction to a pair of opposed, interengaged forming rolls, wherein each forming roll includes a plurality of axially spaced, circumferentially extending, alternating radial teeth and intervening grooves, and wherein the teeth of one roll are opposite from and extend into the grooves of the opposed roll; and
   b. passing said web between said forming rolls while said web is at a temperature of about 25° C. to about 120° C. and an engineering strain rate of about 50 $s^{-1}$ to about 1650 $s^{-1}$, and mechanically modifying said web to form a breathable web having an MVTR of at least about 2000 g/m²/24 hr, a dynamic fluid impact value of less than about 10 g/m², a bubble pressure of at least about 45 psi, and an air flow of at least about 2 liters/m²/s.

2. The method in accordance with claim 1 wherein the engineering strain rate ranges from about 160 $s^{-1}$ to about 1100 $s^{-1}$.

3. The method in accordance with claim 1 wherein the engineering strain rate ranges from about 350 $s^{-1}$ to about 900 $s^{-1}$.

4. The method in accordance with claim 1 wherein the precursor web has a web speed of from about 30 to about 365 m/min in step (b).

5. The method in accordance with claim 1 wherein the teeth and grooves of each forming roll are circumferentially continuous.

6. The method in accordance with claim 1 wherein the teeth of at least one of the forming rolls include a plurality of spaced, circumferential recesses.

7. A method of making a breathable composite web comprising:
   a. joining a nonwoven web to a polymeric film having a pore forming agent dispersed therein to form a composite web;
   b. feeding said composite web in a web movement direction to a pair of opposed, interengaged forming rolls, wherein each forming roll includes a plurality of axially spaced, circumferentially extending, alternating radial teeth and intervening grooves, and wherein the teeth of one roll are opposite from and extend into the grooves of the opposed roll; and
   c. passing said composite web between said forming rolls while said composite web is at a temperature of about 25° C. to about 120° C. and an engineering strain rate of about 50 $s^{-1}$ to about 1650 $s^{-1}$ and mechanically modifying said composite web to form a breathable composite web having an MVTR of at least about 2000 g/m²/24 hr, a dynamic fluid impact value of less than about 10 g/m², and a bubble pressure of at least about 45 psi.

8. The method in accordance with claim 7 wherein the engineering strain rate ranges from about 160 $s^{-1}$ to about 1100 $s^{-1}$.

9. The method in accordance with claim 7 wherein the engineering strain rate ranges from about 350 $s^{-1}$ to about 900 $s^{-1}$.

10. The method in accordance with claim 7 wherein the composite web has a web speed of from about 30 to about 365 m/min in step (c).

11. The method in accordance with claim 7 wherein the teeth and grooves of each forming roll are circumferentially continuous.

12. The method in accordance with claim 7 wherein the teeth of at least one of the forming rolls include a plurality of spaced, circumferential recesses.

13. The method in accordance with claim 7 wherein the film is modified to increase its breathability before being joined to the nonwoven web.

14. The method in accordance with claim 7 wherein the nonwoven web and the film are joined by an adhesive.

15. The method in accordance with claim 7 wherein the nonwoven web and the film are joined by extrusion coating the nonwoven web with the film.

* * * * *